(12) United States Patent
Kitajima

(10) Patent No.: US 7,393,103 B2
(45) Date of Patent: Jul. 1, 2008

(54) OPERATION MICROSCOPE APPARATUS

(75) Inventor: Nobuaki Kitajima, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 259 days.

(21) Appl. No.: 11/406,378

(22) Filed: Apr. 19, 2006

(65) Prior Publication Data

US 2006/0238711 A1 Oct. 26, 2006

(30) Foreign Application Priority Data

Apr. 21, 2005 (JP) ............................. 2005-124059

(51) Int. Cl.
*A61B 3/10* (2006.01)
(52) U.S. Cl. .................. 351/216; 351/214; 351/221
(58) Field of Classification Search ................. 351/205, 351/214, 216, 221
See application file for complete search history.

(56) References Cited

U.S. PATENT DOCUMENTS 5,506,634 A * 4/1996 Wei et al. ..................... 351/221

6,937,390 B2 * 8/2005 Akiyama et al. ............. 359/381

FOREIGN PATENT DOCUMENTS

| JP | 2003-62003 | 3/2003 |
|----|------------|--------|
| JP | 2005-107951 | 4/2005 |

* cited by examiner

*Primary Examiner*—Huy K Mai
(74) *Attorney, Agent, or Firm*—Edwards Angell Palmer & Dodge LLP

(57) ABSTRACT

Provided is an operation microscope apparatus for easily and speedily obtaining a suitable separation state between illumination light and observation light in a case where a front lens is replaced by another one. An illumination optical system includes a slit plate in which slit holes having different slit widths are formed. Each of a plurality of front lens having different refractive powers is integrally formed with corresponding one of storing sections. One of the storing sections is attached to an elevation regulating member. The elevation regulating member includes micro-switches. Each of the storing sections includes a protruding portion for turning on corresponding one of the micro-switches at the time of attachment. A control unit sets an illumination angle of the illumination light and a slit width of a slit based on a detection signal from a micro-switch which becomes an on state.

44 Claims, 15 Drawing Sheets

FIG. 3A FRONT LENS=40D
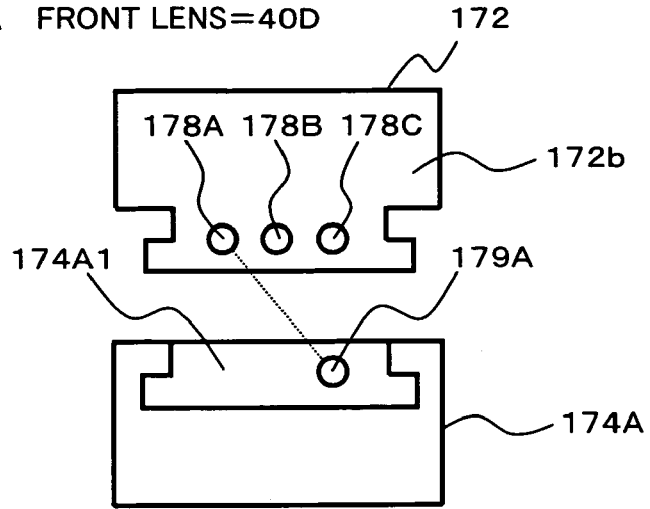
FIG. 3B FRONT LENS=80D
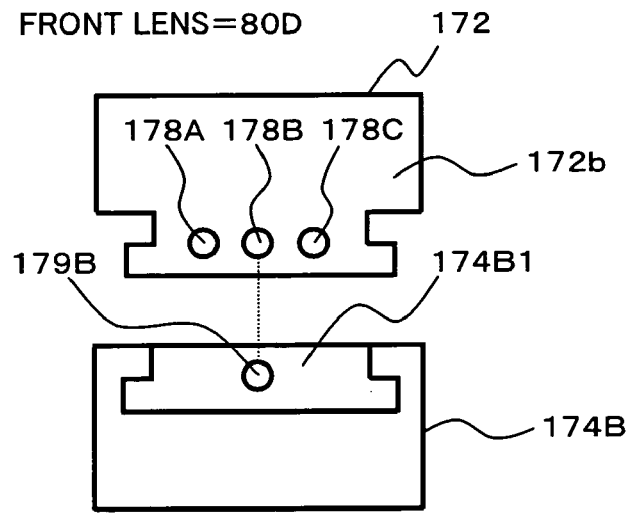
FIG. 3C FRONT LENS=120D
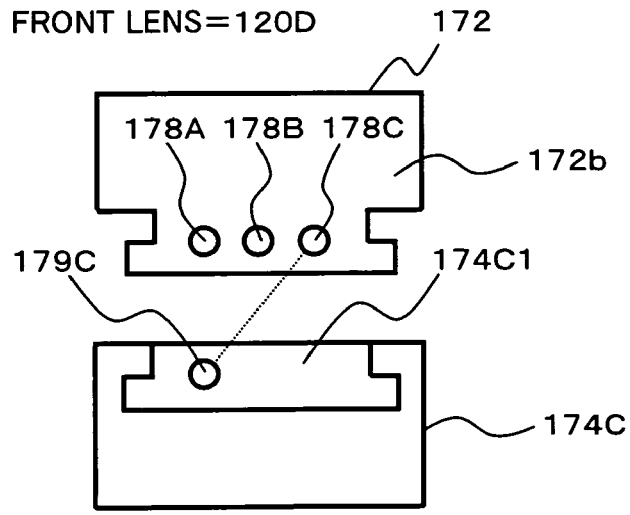

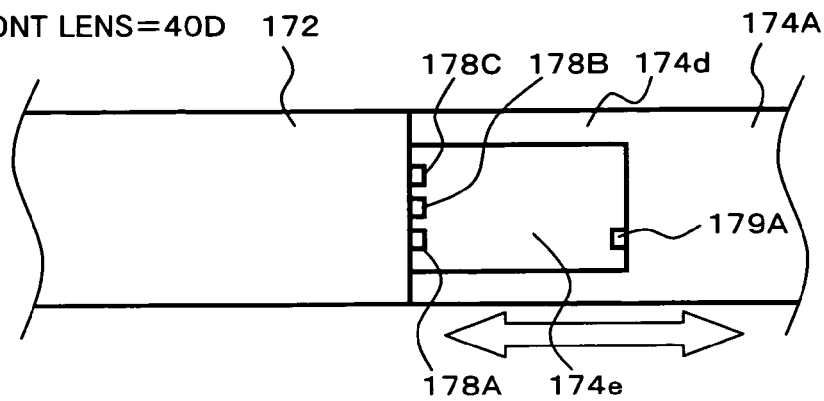
FIG. 4A FRONT LENS=40D
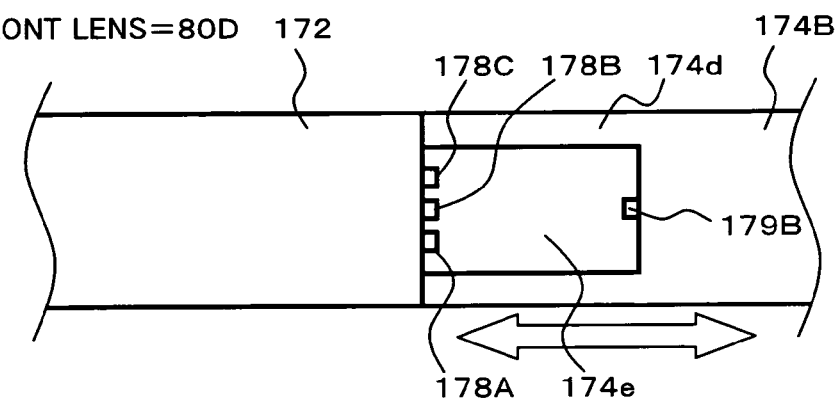
FIG. 4B FRONT LENS=80D
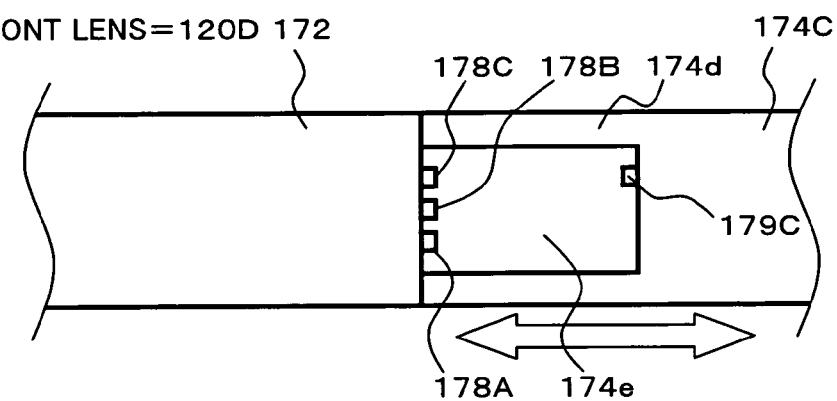
FIG. 4C FRONT LENS=120D ( OPERATOR SIDE )

FIG. 10

ILLUMINATION ANGLE INFORMATION 62A

| REFRACTIVE POWER OF FRONT LENS | 40 D | 80 D | 120 D | NO POWER |
|---|---|---|---|---|
| ILLUMINATION ANGLE (DEGREES) | 4 | 7 | 7 | 4 or 7 |

FIG. 11

SLIT WIDTH INFORMATION 62B

| REFRACTIVE POWER OF FRONT LENS | 40 D | 80 D | 120 D | NO POWER |
|---|---|---|---|---|
| SLIT WIDTH 9mm | ○ | × | × | ○ |
| 5mm | ○ | ○ | × | ○ |
| 2.5mm | × | ○ | ○ | ○ |

ON OBJECTIVE LENS 15          T ILLUMINATION OPTICAL PATH

QL
OBSERVATION OPTICAL
PATH OF LEFT OBSERVATION
OPTICAL SYSTEM

QR
OBSERVATION OPTICAL
PATH OF RIGHT OBSERVATION
OPTICAL SYSTEM ( OPERATOR SIDE )

ON CORNEA Ec ( OPERATOR SIDE )

ON OBJECTIVE LENS 15    T ILLUMINATION OPTICAL PATH

QL
OBSERVATION OPTICAL
PATH OF LEFT OBSERVATION
OPTICAL SYSTEM

QR
OBSERVATION OPTICAL
PATH OF RIGHT OBSERVATION
OPTICAL SYSTEM (OPERATOR SIDE)

ON CORNEA Ec (OPERATOR SIDE)

OPERATION MICROSCOPE APPARATUS

BACKGROUND OF THE INVENTION

1. Field of the Invention

The present invention relates to an operation microscope apparatus used for an ophthalmologic operation, and more particularly, to an operation microscope apparatus including a front lens for condensing illumination light to illuminate an interior of an eye.

2. Description of the Related Art

Up to now, when a retina and vitreous body operation in an ophthalmologic field is performed, as shown in FIG. 13, an operation contact lens 200 is placed on a cornea Ec of an eye to be operated E. Then, while a light guide (optical fiber) 201 is inserted into an interior of the eye to illuminate an operation region, an operation instrument 202 such as a cutter or a forceps is inserted into the interior of the eye to perform the operation. In FIG. 13, reference symbol Ec denotes the cornea and Ev denotes a vitreous chamber. When the operation is to be performed using the operation method as shown in FIG. 13, it is necessary that an operator hold the light guide 201 in his/her one hand and hold the operation instrument 202 in his/her other hand. This raises a problem in that, for example, it is difficult to perform a fine operation.

In order to deal with the problem, there has been proposed an operation microscope apparatus using a front lens for illuminating the interior of the eye to be operated with illumination light condensed between the eye to be operated and a front focus position of an objective lens (see, for example, JP 2003-062003 A). A plurality of front lenses whose refractive powers are different from one another is prepared. A suitable front lens is selected corresponding to, for example, an observation position of a fundus Er of the eye and attached to the operation microscope apparatus.

FIG. 14 shows an external structure of an operation microscope apparatus 100 using a front lens. The operation microscope apparatus 100 includes a pillar 2 for supporting the operation microscope apparatus 100, a first arm 3 whose one end is connected with an upper end of the pillar 2, a second arm 4 whose one end is connected with the other end of the first arm 3, a drive device 5 connected with the other end of the second arm 4, an operator's microscope 6 suspended from the drive device 5, an assistant's microscope 7 provided adjacent to the operator's microscope 6, and a foot switch 8 for performing various manipulations by a foot. The operator's microscope 6 and the assistant's microscope 7 are three-dimensionally moved in a longitudinal direction and a lateral direction by the drive device 5 in response to manipulation performed by an operator or the like.

The operator's microscope 6 includes a lens barrel section 10 housing, for example, various optical systems and various drive systems. An inverter section 12 housing a known optical unit (image erecting prism) for converting an observation image obtained as an inverted image into an erect image is provided on an upper portion of the lens barrel section 10. A pair of left and right eyepiece sections 11L and 11R are provided on an upper portion of the inverter section 12. The operator looks through the eyepiece sections 11L and 11R to observe the eye to be operated E with both eyes.

The operator's microscope 6 is connected with a front lens 13 through a holding arm 14. The holding arm 14 includes an upper end portion provided to be pivotable in a longitudinal direction, so that the front lens 14 can be removed from a position between the eye to be operated E and a front focus position of an objective lens (not shown). The front lens 13 and the holding arm 14 are stored in a storing section (not shown).

When an eye with the natural lens (phakia) or an eye with the implanted intraocular lens (pseudophakia) is an observation object, relatively weak reflection light on the natural lens or the intraocular lens (IOL) causes a reduction in sharpness of the observation image. Dispersion light from a sclera causes a reduction in contrast of the observation image.

In view of this, it is desirable that the operation microscope apparatus have, for example, (1) a function capable of adjusting a size of an illumination filed and a shape thereof, (2) a function capable of shifting the illumination field, and (3) a function capable of adjusting an angle (illumination angle) between an optical axis (observation optical axis) of an observation optical system and an optical axis (illumination optical axis) of an illumination optical system. In order to realize the functions (1) and (2), there has been known a method of illuminating the interior of the eye with slit light from a slit mechanism incorporated in the illumination optical system (see, for example, JP 2003-062003 A).

FIG. 15 shows a structure of an optical system of the above-mentioned operation microscope apparatus. In the case of the operation microscope apparatus 100 shown in FIG. 14, the optical system is housed in the lens barrel section 10 of the operator's microscope 6 and includes an illumination optical system 20 and a pair of right and left observation optical systems 30. Note that FIG. 15 is a side view showing the optical system as viewed from the assistant's microscope 7 side.

The pair of right and left observation optical systems 30 are provided so as to sandwich an optical axis O of an objective lens 15 on both ends thereof. Each of the right and left observation optical systems 30 includes a zoom lens system 31, a beam splitter 32, an imaging lens 33, an image erecting prism 34, an interpupillary distance adjusting prism 35, a field stop 36, and an eyepiece 37. The zoom lens system 31 is composed of a plurality of zoom lenses 31a, 31b, and 31c. The beam splitter 32 is used to separate a part of observation light exited from the eye to be operated E from the other part thereof to lead the separated part to the assistant's microscope 7 or a TV camera (not shown).

The illumination optical system 20 includes an illumination light source 21, a condenser lens 22, an illumination field stop 23, a slit plate 24, an illumination prism 25, and a collimator lens 27.

The slit plate 24 has a slit hole 24a formed therein. The slit plate 24 can be inserted to and removed from an illumination optical path of the illumination optical system 20. In particular, when the slit plate 24 is to be inserted to the illumination path, the slit plate 24 is moved in a direction orthogonal to an illumination optical axis O'. The slit hole 24a is formed in a direction orthogonal to both the illumination optical axis O' and a movable direction of the slit plate 24. An image projected onto the fundus of the eye is extended in parallel with a plane including the right and left observation optical axes of the right and left observation optical systems 30.

The illumination field stop 23 is provided in a position optically conjugate with a front focus position F of the objective lens 15. The slit plate 24 is provided near the illumination field stop 23. The slit hole 24a is formed in a position substantially optically conjugate with the front focus position F of the objective lens 15. The objective lens 15 is disposed such that the front focus position F becomes conjugate with the fundus Er (retina) of the eye.

The illumination light source 21 can be housed in the lens barrel section 10 of the operator's microscope 6 or provided outside the lens barrel section 10 to guide the illumination light to the condenser lens 22 of the lens barrel section 10 through an optical fiber.

In order to prevent reflection light of the illumination light on the surface of an operation contact lens or the cornea from entering the observation optical system to cause glare, a structure in which an illumination optical path and an observation optical path are separated from each other on an interface surface on which the reflection light is produced is employed for the conventional operation microscope apparatus.

FIGS. 16A and 16B show suitable separation states in which the illumination optical path and the observation optical path are separated from each other in the cornea Ec of the eye to be operated E. Here, FIG. 16A shows the case where a front lens 13A whose refractive power is 40 diopters (D) is used and FIG. 16B shows the case where a front lens 13B whose refractive power is 80 D is used. FIGS. 17A and 17B show the cases where the separation state shown in FIG. 16A is viewed from above the observation optical system 30. FIGS. 18A and 18B show the cases where the separation state shown in FIG. 16B is viewed from above the observation optical system 30.

The front lens 13A of 40 D as shown in FIG. 16A is used when the fundus Er of the eye and vicinities thereof are observed. Illumination light 301 condensed by the front lens 13A passes through a region 301a on the cornea Ec which is distant from the optical axis O of the objective lens 15 and is incident on the interior of the eye, thereby illuminating the fundus Er of the eye and the vicinities thereof. On the other hand, reflection light (observation light) 401 of the illumination light 301 on the fundus Er of the eye and the vicinities thereof exits from the interior of the eye through a region 401a including the optical axis O of the objective lens 15 and travels to the front lens 13A. Here, it is necessary to provide the region 301a on the cornea Ec through which the illumination light 301 passes and the region 401a through which the observation light 401 passes so as not to overlap with each other, thereby preventing cornea reflection light of the illumination light 301 from mixing with the observation light 401.

At this time, an illumination optical path T and left and right observation optical paths QL and QR in the optical lens 15 become a separation state as shown in FIG. 17A. In the cornea Ec, the region 301a through which the illumination light passes, a region 401aL through which the observation light 401 to be incident on the left observation optical system passes, and a region 401aR through which the observation light 401 to be incident on the right observation optical system passes become a separation state as shown in FIG. 17B.

On the other hand, the front lens 13B of 80 D as shown in FIG. 16B is used when a region distant from the fundus Er of the eye is observed. Even in such a case, it is necessary to provide a region 302a on the cornea Ec through which illumination light 302 passes and a region 402a through which the observation light 402 passes so as not to overlap with each other, thereby preventing cornea reflection light of the illumination light 302 from mixing with the observation light 402.

At this time, the illumination optical path T and left and right observation optical paths QL and QR in the optical lens 15 become a separation state as shown in FIG. 18A. In the cornea Ec, a region 302a through which the illumination light passes, a region 402aL through which the observation light 402 to be incident on the left observation optical system passes, and a region 402aR through which the observation light 402 to be incident on the right observation optical system passes become a separation state as shown in FIG. 18B.

When the operation contact lens is used, although not shown, it is necessary to separate a region on the surface thereof through which the illumination light passes and a region on the surface thereof through which the observation light passes from each other. In addition to this, it is necessary to separate a region on the cornea through which the illumination light passes and a region on the cornea through which the observation light passes from each other.

When the eye to be operated E is significantly displaced in the optical axis O direction of the objective lens 15, the separation state between the illumination light and the observation light is broken. Therefore, it is necessary to ensure the suitable separation states as shown in FIGS. 16A, 16B, 17A, 17B, 18A and 18B in view of the amount of displacement of the eye to be operated E, which moves for the operation.

In the conventional operation microscope apparatus, the separation states are manually ensured by an operation or the like. However, for example, when the operator is not a skilled operator, it is difficult to realize the suitable separation states.

As shown in each of FIGS. 16A and 16B, the suitable separation state between the illumination light and the observation light is changed corresponding to the refractive power of the front lens 13 (13A or 13B). Therefore, every time the front lens 13 is replaced by another one, it is necessary to adjust an illumination angle of the illumination light and a slit width to ensure the suitable separation state, so that the manipulation is troublesome. When the front lens 13 is replaced by another one for the operation, it takes a time to ensure the separation state, with the result that it is likely to unnecessarily prolong the operation.

SUMMARY OF THE INVENTION

The present invention has been made in view of the above-mentioned circumstances. An object of the present invention is to provide an operation microscope apparatus capable of easily and speedily obtaining a suitable separation state between illumination light and observation light in a case where a front lens is replaced by another one.

In order to achieve the above-mentioned object, according to a first aspect of the present invention, an operation microscope apparatus is characterized by including: an illumination optical system for emitting illumination light to an eye to be operated at a predetermined illumination angle; an objective lens; a front lens for condensing the illumination light from the illumination optical system to illuminate an interior of the eye to be operated, the front lens being provided in a use position between the eye to be operated and a front focus point of the objective lens in which a plurality of front lenses having different refractive powers are selectively located; an observation optical system including an eyepiece, for guiding, to the eyepiece, reflection light of the illumination light from the eye to be operated through the front lens and the objective lens; input means for inputting identification information for identifying the front lens located in the use position, of the plurality of front lenses; and control means for controlling the illumination optical system to set an illumination angle of the illumination light to an illumination angle corresponding to the inputted identification information. When the identification information for identifying the front lens located in the use position, of the plurality of front lenses is inputted, the illumination angle of the illumination light is automatically set to the illumination angle corresponding to the identification information. Therefore, there is an effect in that a suitable separation state between illumination light and observation light can be easily and speedily obtained corresponding to the used front lens.

According to a second aspect of the present invention, an operation microscope apparatus is characterized by including: an illumination optical system for emitting illumination light to an eye to be operated at a predetermined illumination angle, the illumination optical system including slit means for adjusting a slit width of a slit for transmitting a part of the illumination light, the slit being formed in the slit means; an objective lens; a front lens for condensing the illumination light from the illumination optical system to illuminate an interior of the eye to be operated, the front lens being provided in a use position between the eye to be operated and a front focus point of the objective lens in which a plurality of front lenses having different refractive powers are selectively located; an observation optical system including an eyepiece, for guiding, to the eyepiece, reflection light of the illumination light from the eye to be operated through the front lens and the objective lens; input means for inputting identification information for identifying the front lens located in the use position, of the plurality of front lenses; and control means for controlling the slit means to set the slit width of the slit to a slit width corresponding to the inputted identification information. When the identification information for identifying the front lens located in the use position, of the plurality of front lenses is inputted, the slit width of the slit is automatically set to a slit width corresponding to the identification information. Therefore, there is an effect in that a suitable separation state between illumination light and observation light can be easily and speedily obtained corresponding to the used front lens.

According to a third aspect of the present invention, an operation microscope apparatus is characterized by including: an illumination optical system for emitting illumination light to an eye to be operated at a predetermined illumination angle, the illumination optical system including slit means for adjusting a slit width of a slit for transmitting a part of the illumination light, the slit being formed in the slit means; an objective lens; a front lens for condensing the illumination light from the illumination optical system to illuminate an interior of the eye to be operated, the front lens being provided in a use position between the eye to be operated and a front focus point of the objective lens in which a plurality of front lenses having different refractive powers are selectively located; an observation optical system including an eyepiece, for guiding, to the eyepiece, reflection light of the illumination light from the eye to be operated through the front lens and the objective lens; input means for inputting identification information for identifying the front lens located in the use position, of the plurality of front lenses; and control means for controlling the illumination optical system to set an illumination angle of the illumination light to an illumination angle corresponding to the inputted identification information and controlling the slit means to set the slit width of the slit to a slit width corresponding to the inputted identification information. When the identification information for identifying the front lens located in the use position, of the plurality of front lenses is inputted, the illumination angle of the illumination light is automatically set to the illumination angle corresponding to the identification information and the slit width of the slit is automatically set to a slit width corresponding to the identification information. Therefore, there is an effect in that a suitable separation state between illumination light and observation light can be easily and speedily obtained corresponding to the used front lens.

BRIEF DESCRIPTION OF THE DRAWINGS

In the accompanying drawings:

FIGS. 1A and 1B are schematic side views showing an example of a connection mode of a front lens with an operator's microscope in an operation microscope apparatus according to an embodiment of the present invention, in which FIG. 1A shows a state in which the front lens is located in a use position and FIG. 1B shows a state in which the front lens is located in a storing position;

FIGS. 2A and 2B are schematic views showing an example of a connection mode of a storing section with an elevation regulating member in the operation microscope apparatus according to the embodiment of the present invention, in which FIG. 2A is a cross sectional view showing the elevation regulating member and the storing section and FIG. 2B is a side view showing the elevation regulating member and the storing section;

FIGS. 3A to 3C are schematic structural views showing micro-switches of the elevation regulating member and protruding portions of the storing section in the operation microscope apparatus according to the embodiment of the present invention, in which FIG. 3A shows a case where a front lens whose refractive power is 40 diopters is used, FIG. 3B shows a case where a front lens whose refractive power is 80 diopters is used, and FIG. 3C shows a case where a front lens whose refractive power is 120 diopters is used;

FIGS. 4A to 4C are schematic structural views showing the micro-switches of the elevation regulating member and the protruding portions of the storing section in the operation microscope apparatus according to the embodiment of the present invention, in which FIG. 4A shows the case where the front lens whose refractive power is 40 diopters is used, FIG. 4B shows the case where the front lens whose refractive power is 80 diopters is used, and FIG. 4C shows the case where the front lens whose refractive power is 120 diopters is used;

FIG. 10 shows an example of illumination angle information for the operation microscope apparatus according to the embodiment of the present invention;

FIG. 11 shows an example of slit width information for the operation microscope apparatus according to the embodiment of the present invention;

FIGS. 16A and 16B each are a schematic view showing a suitable separation state between an illumination optical path and an observation optical path of the operation microscope apparatus on a cornea of an eye to be operated, in which FIG. 16A shows the case where the front lens whose refractive power is 40 diopters is used and FIG. 16B shows the case where the front lens whose refractive power is 80 diopters is used;

FIGS. 17A and 17B each are a schematic view showing a suitable separation state between the illumination optical path and each of observation optical paths of the operation microscope apparatus, in which FIG. 17A shows a separation state between the illumination optical path and each of right and left observation optical paths on an objective lens in the case where the front lens whose refractive power is 40 diopters is used and FIG. 17B shows a separation state between the illumination optical path and each of the right and left observation optical paths on the cornea of the eye to be operated in the case where the front lens whose refractive power is 40 diopters is used; and FIGS. 18A and 18B each are a schematic view showing a suitable separation state between the illumination optical path and each of the observation optical paths of the operation microscope apparatus, in which FIG. 18A shows a separation state between the illumination optical path and each of the right and left observation optical paths on the objective lens in the case where the front lens whose refractive power is 80 diopters is used and FIG. 18B shows a separation state between the illumination optical path and each of the right and left observation optical paths on the cornea of the eye to be operated in the case where the front lens whose refractive power is 80 diopters is used.

DETAILED DESCRIPTION OF THE PREFERRED EMBODIMENT

Examples of operational microscope apparatuses according to a preferred embodiment of the present invention will be described in detail with reference to the drawings.

First Embodiment

[External Structure]

Figure 14:
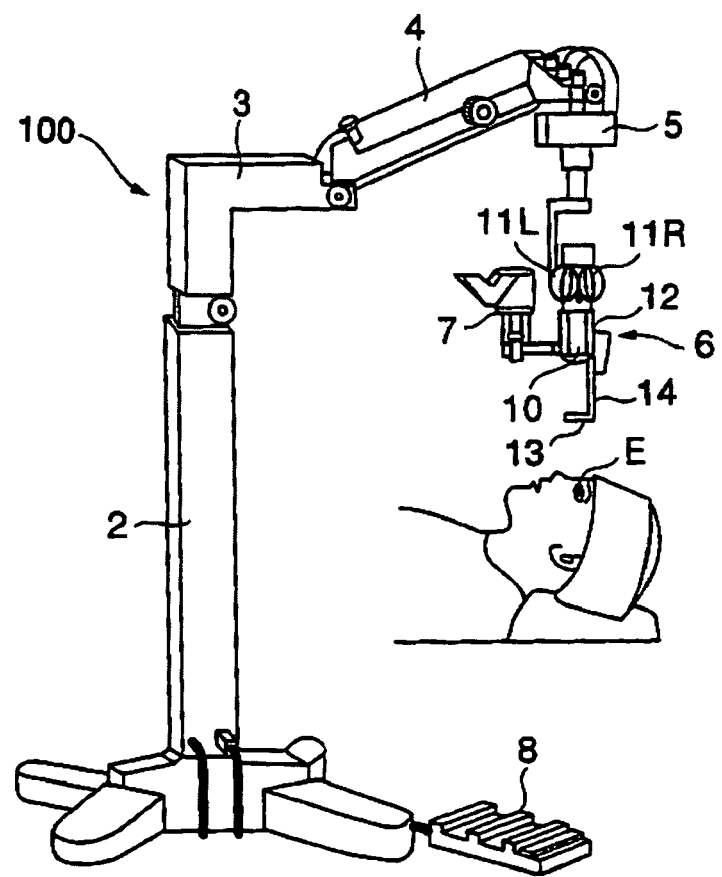
FIG. 14 is a schematic view showing an external structure of a conventional operation microscope apparatus.

An operation microscope apparatus according to a first embodiment of the present invention has the same external structure as that of a conventional operation microscope apparatus (see FIG. 14). An operation microscope apparatus 1 according to the first embodiment of the present invention includes a pillar 2 for supporting the operation microscope apparatus 1, a first arm 3 whose one end is connected with an upper end of the pillar 2, a second arm 4 whose one end is connected with the other end of the first arm 3, a drive device 5 connected with the other end of the second arm 4, an operator's microscope 6 suspended from the drive device 5, an assistant's microscope 7 provided adjacent to the operator's microscope 6, and a foot switch 8 for performing various manipulations by a foot.

The operator's microscope 6 includes a main body section 6a, a lens barrel section 10 housing, for example, various optical systems and various drive systems. An inverter section 12 housing an optical unit (image erecting prism) for converting an observation image obtained as an inverted image into an erect image is provided on an upper portion of the lens barrel section 10. A pair of left and right eyepiece sections 11L and 11R are provided on an upper portion of the inverter section 12.

The operator's microscope 6 is connected with a front lens 13 through a holding arm 14. The front lens 13 is disposed in a position between an eye to be operated E and a front focus position of an objective lens 15 (hereinafter referred to as a "use position"), so that an interior of the eye to be operated E is illuminated with condensed illumination light. A plurality of front lenses having different refractive powers (such as 40 D, 80 D and 120 D) are prepared for the front lens 13 and a lens to be used is selected corresponding to an observation area. An attachment and detachment mode of the front lens 13 will be described later.

Figure 1A:
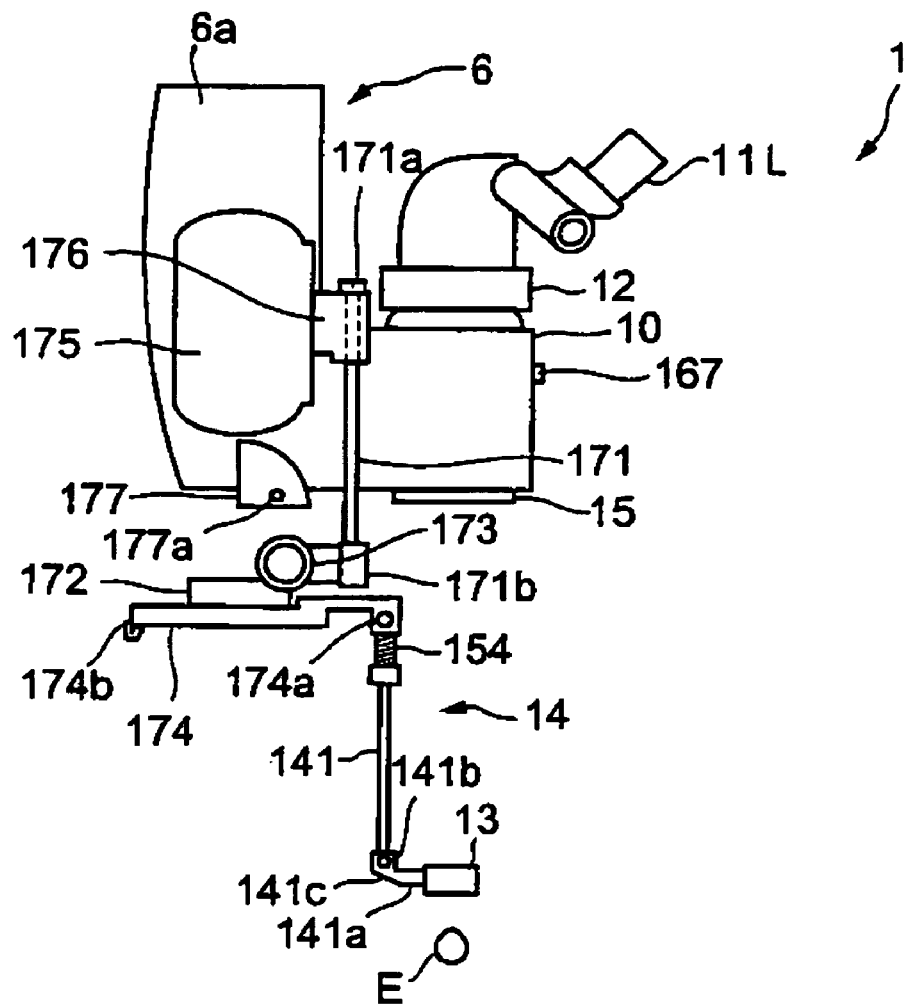
Figure 1B:
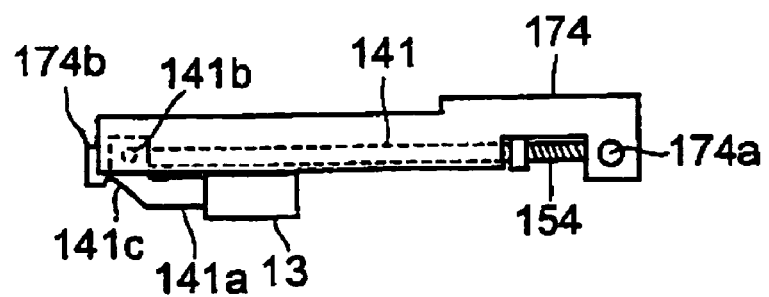

FIGS. 1A and 1B show a connection mode of the front lens 13 with the operator's microscope 6. The objective lens 15 is provided to a lower end of the lens barrel section 10. Switches 167 manipulated to select a front lens 13 to be used from the plurality of front lenses 13 having the different refractive powers are provided on an operator's side surface of the lens barrel section 10. The number of switches 167 is equal to the number of front lenses 13. For example, three switches are provided. An operator manipulates a switch 167 associated with the front lens 13 to be used to input information indicating that the associated front lens 13 is used. The switches 167 are not limited to such a structure. Therefore, a switch capable of selecting a front lens to be used from the plurality of front lenses 13, for example, another type of switch such as a dial type switch may be provided. Each of the switches 167 is covered with a detachable sterilized cap, thereby preventing bacteria from being transmitted to a patient for the operation.

The front lens 13 is held by a holding plate 141a which is formed so as to surround the circumference thereof. The holding plate 141a is connected with an arm section 141 through a pivot 141b to be pivotable about the pivot 141b. The holding plate 141a has an oblique portion 141c formed therein.

A coil spring 154 is wound around an upper portion of the arm section 141. The upper portion of the arm section 141 is connected with an end of a storing section 174 by a pivot 174a. A front lens manipulation knob (not shown) extended in a lateral direction as viewed from the operator's side is provided on the arm section 141. The operator can pivot the holding arm 14 about the pivot 174a with the front lens manipulation knob to locate the front lens 13 in the use position or a storing position described later.

The operator's microscope 6 further includes an elevating arm 171 having a fringe portion 171a provided on the upper side thereof, a connecting portion 171b connected with a lower portion of the elevating arm 171, an elevation regulating member 172 connected with the connecting portion 171b, a connecting knob 173 extended through the connecting portion 171b, and the storing section 174 for storing the front lens 13 and the holding arm 14.

The operator's microscope 6 further includes a drive section 175 for driving an elevating arm support member 176 for supporting the elevating arm 171, upward and downward. The elevating arm 171 extends through the elevating arm support member 176. The elevating arm 171 is prevented from being separated from the elevating arm support member 176 by the fringe portion 171a. As a result, when the elevating arm support member 176 is moved upward and downward by the drive section 175, the front lens 13 is moved upward and downward in conjunction therewith. Therefore, a distance between the front lens 13 and the objective lens 15 relatively changes.

An elevation regulating member 177 for regulating, for example, an upward movable range of the front lens 13 with the elevation regulating member 172 is bonded to a lower portion of the main body section 6a. The elevation regulating member 177 has a connecting hole 177a formed therein. A connecting knob 173 includes a rotating screw. When the rotating screw is rotated in a predetermined direction, a foot portion thereof is inserted into the connecting hole 177a. Therefore, the front lens 13, the holding arm 14, the storing section 174, and the like are connected with the main body section 6a. The connection with the main body section 6a is performed after the front lens 13 and the like are integrally elevated up by the drive section 175 to align the foot portion of the rotating screw of the connecting knob 173 with the connecting hole 177a.

The front lens 13 shown in FIG. 1A is in a state in which it is inserted into the use position between the eye to be operated E and the objective lens 15, that is, a use state. When the front lens 13 which is in the use state is to be stored, the operator pivots the holding arm 14 upward with the front lens manipulation knob to store the front lens 13 and the holding arm 14 in the storing section 174. On the other hand, when the front lens 13 stored in the storing section 174 is to be used, the operator pivots the holding arm 14 downward in a reverse way.

FIG. 1B shows a state in which the front lens 13 and the holding arm 14 are located in the storing position. The storing section 174 includes a concave storing portion which is formed on the lower side of the storing section 174 and extended in the longitudinal direction thereof. The holding arm 14 is stored in the storing portion. The holding plate 141a is stored with a bent state in which it is pivoted about the pivot 141b. This results from an action between the oblique portion 141c of the holding plate 141a and a contact member 174b bonded to an end portion of the storing section 174. That is, when the arm section 141 is pivoted upward, the oblique portion 141c is in contact with the contact member 174b and the holding plate 141a is guided along the oblique portion 141c to pivot about the pivot 141b. Therefore, the holding plate 141a is automatically bent and stored.

[Attachment and Detachment Mode of Front Lens]

The storing section 174 is formed to be detachably attachable to the elevation regulating member 172. The reason why such a detachably attachable structure is used is that it is necessary to detach the storing section 174 from the operator's microscope 6 when the front lens 13 and the holding arm 14 are sterilized after the operation or the like. The storing section 174, the front lens 13, and components provided therebetween are integrally constructed. Even when the front lens 13 and the like are removed, the operation microscope apparatus 1 can be used as an operation microscope apparatus without the front lens.

Figure 2A:
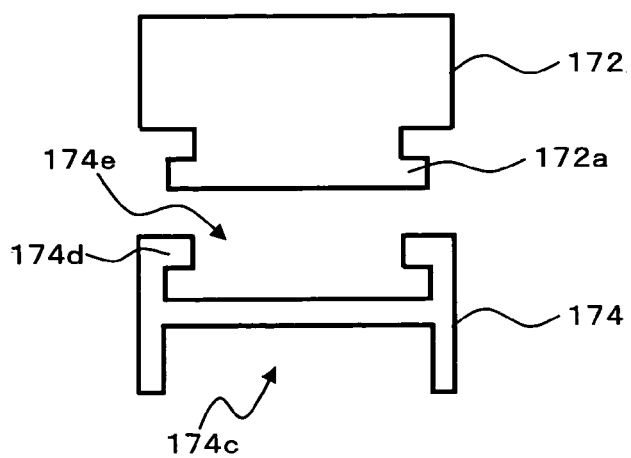
Figure 2B:
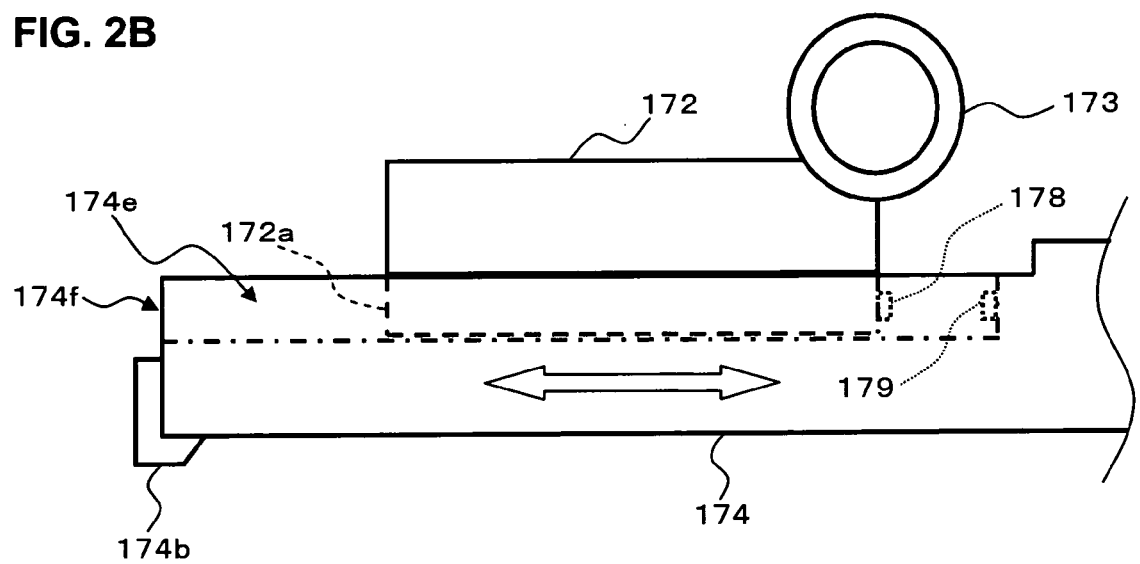

FIGS. 2A and 2B show an example of a connection mode of the storing section 174 with the elevation regulating member 172. The storing section 174 has a shape whose longitudinal direction (length direction) is a direction joining the pivot 174a with the contact member 174b (lateral direction shown in FIG. 1A). The elevation regulating member 172 similarly has a shape whose longitudinal direction (length direction) is the lateral direction shown in FIG. 1A). FIG. 2A is a cross sectional view in the short length direction (width direction), showing the elevation regulating member 172 and the storing section 174. FIG. 2B is a perspective view in the longitudinal direction, showing the elevation regulating member 172 and the storing section 174.

As shown in FIG. 2A, the elevation regulating member 172 includes a fringe-shaped connection rail portion 172a provided on the lower side thereof. The connection rail portion 172a has a rail shape extended in the length direction of the elevation regulating member 172. The connection rail portion 172a further has a fringe provided in the width direction.

The storing section 174 has a storage space 174c for storing the holding arm 14, which is provided on the lower side of the storing section 174. The storing section 174 includes a concave connection rail support 174e which is formed on the upper side thereof and extended in the length direction. The connection rail support 174e includes a protruding portion 174d which protrudes from both sides in the width direction on the upper surface of the storing section 174 to an inner side direction and extends in the length direction.

When the storing section 174 is to be attached to the elevation regulating member 172, an end portion of the connection rail support 174e of the storing section 174, which is located on a contact member 174b side is aligned with an end portion of the connection rail portion 172a of the elevation regulating member 172, which is located on a connecting knob 173 side. Then, the connection rail support 174e is moved toward the contact member 174b so as to insert the connection rail portion 172a into the connection rail support 174e.

On the other hand, when the storing section 174 is to be detached from the elevation regulating member 172, the connection rail support 174e is moved toward the pivot 174a.

As shown in FIG. 2B, a micro-switch 178 is provided on an end surface of the elevation regulating member 172, which is located on the connecting knob 173 side. A protruding portion 179 is provided on an end surface of the connection rail support 174e of the storing section 174, which is located on a pivot 174a side.

As described above, the plurality of front lenses having different refractive powers are prepared for the front lens 13. Hereinafter, the front lens 13 having a refractive power of 40 D is expressed as a front lens 13A. The front lens 13 having a refractive power of 80 D is expressed as a front lens 13B. The front lens 13 having a refractive power of 120 D is expressed as a front lens 13C.

The front lens 13, the storing section 174, and the like are integrally constructed. Therefore, the storing section 174 integrally provided with the front lens 13A is expressed as a storing section 174A. The storing section 174 integrally provided with the front lens 13B is expressed as a storing section 174B. The storing section 174 integrally provided with the front lens 13C is expressed as a storing section 174C.

FIGS. 3A to 3C and 4A to 4C correspond to the structures with respect to the micro-switch 178 of the elevation regulating member 172 and the protruding portion 179 of each of the storing sections 174A, 174B and 174C. FIGS. 3A and 4A correspond to the case where the front lens 13A having the refractive power of 40 D is used. FIGS. 3B and 4B correspond to the case where the front lens 13B having the refractive power of 80 D is used. FIGS. 3C and 4C correspond to the case where the front lens 13C having the refractive power of 120 D is used.

The micro-switch 178 of the elevation regulating member 172 includes three micro-switches 178A, 178B and 178C which are provided on an end surface 172b of the elevation regulating member 172, which is located on the connecting knob 173 side. The three micro-switches 178A, 178B and 178C are arranged straight in the width direction of the elevation regulating member 172.

On the other hand, the single protruding portion 179 is provided on the end surface of the connection rail support 174e, which is located on the pivot 174a side, of the storing section 174 integrally provided with the front lens 13. As shown in FIGS. 3A and 4A, a protruding portion 179A of the storing section 174A integrally provided with the front lens 13A is located in a position corresponding to the micro-switch 178A of the elevation regulating member 172. As shown in FIGS. 3B and 4B, a protruding portion 179B of the storing section 174B integrally provided with the front lens 13B is located in a position corresponding to the micro-switch 178B of the elevation regulating member 172. As shown in FIGS. 3C and 4C, a protruding portion 179C of the storing section 174C integrally provided with the front lens 13C is located in a position corresponding to the micro-switch 178C of the elevation regulating member 172.

When the storing section 174A is to be attached to the elevation regulating member 172, as shown in FIG. 4A, the protruding portion 179A of the storing section 174A is moved toward the micro-switch 178A of the elevation regulating member 172 and finally collides with the micro-switch 178A to turn on the micro-switch 178A. At this time, the micro-switches 178B and 178C remain in an off state. When the storing section 174B is to be attached to the elevation regulating member 172, as shown in FIG. 4B, the protruding portion 179B of the storing section 174B is moved toward the micro-switch 178B and turns on the micro-switch 178B. At this time, the micro-switches 178A and 178C remain in the off state. When the storing section 174C is to be attached to the elevation regulating member 172, as shown in FIG. 4C, the protruding portion 179C of the storing section 174C is moved toward the micro-switch 178C and turns on the micro-switch 178C. At this time, the micro-switches 178A and 178B remain in the off state.

Each of the micro-switches 178A, 178B and 178C outputs an electrical signal (detection signal) at a time when it is turned ON by corresponding one of the protruding portions 179A, 179B and 179C. At this time, the micro-switches 178A, 178B and 178C output different detection signals. The outputted detection signal is inputted in a control unit described later.

The detection signal outputted from each of the micro-switches 178A, 178B and 178C has, for example, different voltage level or the different number of pulses. The detection signal is outputted to determine which one of the front lenses 13A to 13C is to be used (that is, which is located in the use position). The detection signal corresponds to an example of "identification information" in the present invention.

Each of the micro-switches 178A, 178B and 178C corresponds to an example of "input means" for inputting the detection signal in the control unit described later, in the present invention.

Each of the protruding portions 179A, 179B and 179C corresponds to an example of "input instruction means" in the present invention and acts to selectively turn on the micro-switches 178A, 178B and 178C to output the detection signal for identifying one of the front lenses 13A to 13C which is to be used in the control unit described later. At this time, each of the micro-switches 178A, 178B and 178C corresponds to an example of "detection means" for detecting a detection signal input instruction caused by corresponding one of the protruding portions 179A, 179B and 179C, in the present invention.

[Structures of Optical Systems]

Figure 5:
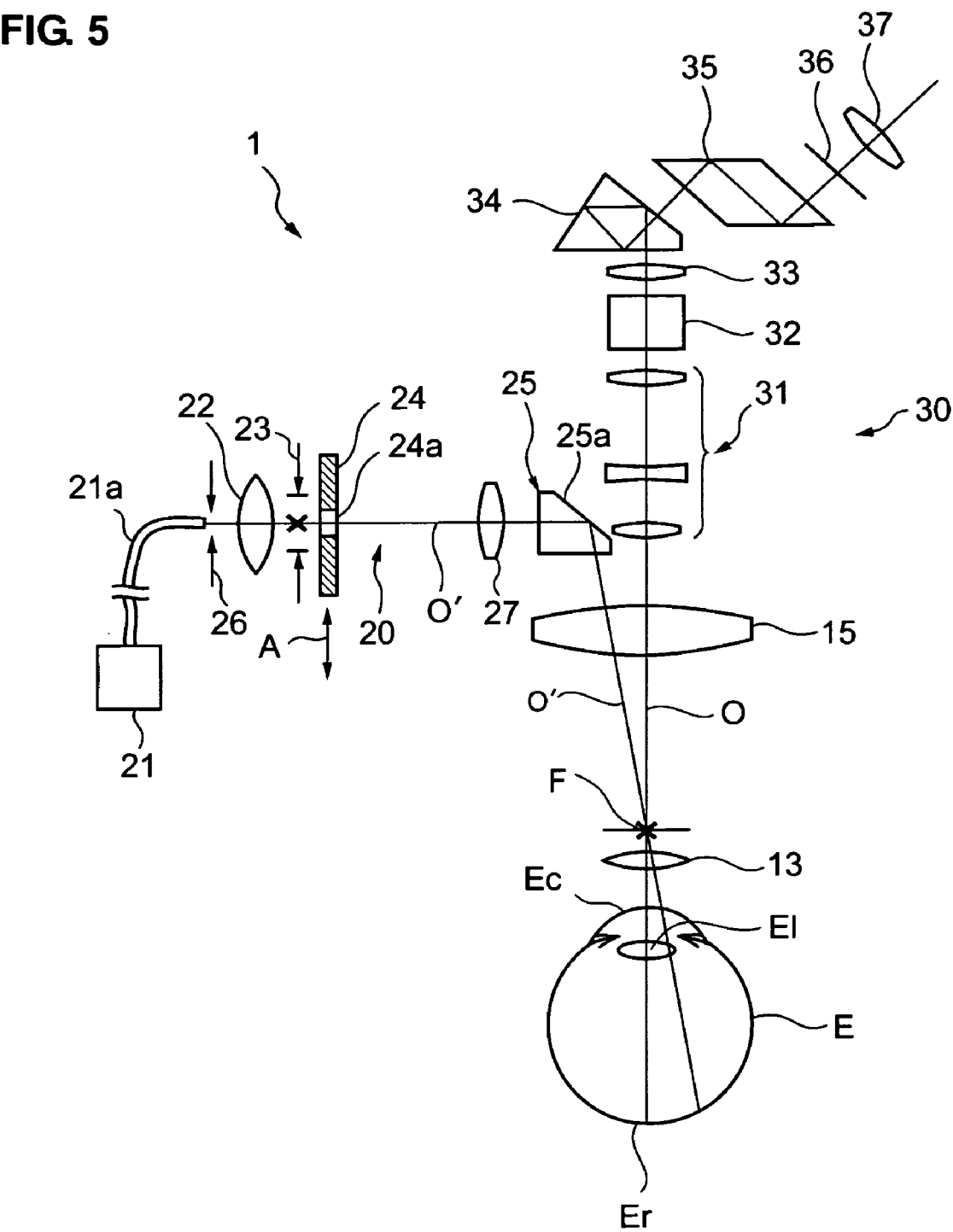
FIG. 5 is a schematic side view showing a structure of an optical system of the operation microscope apparatus according to the embodiment of the present invention.
Figure 6:
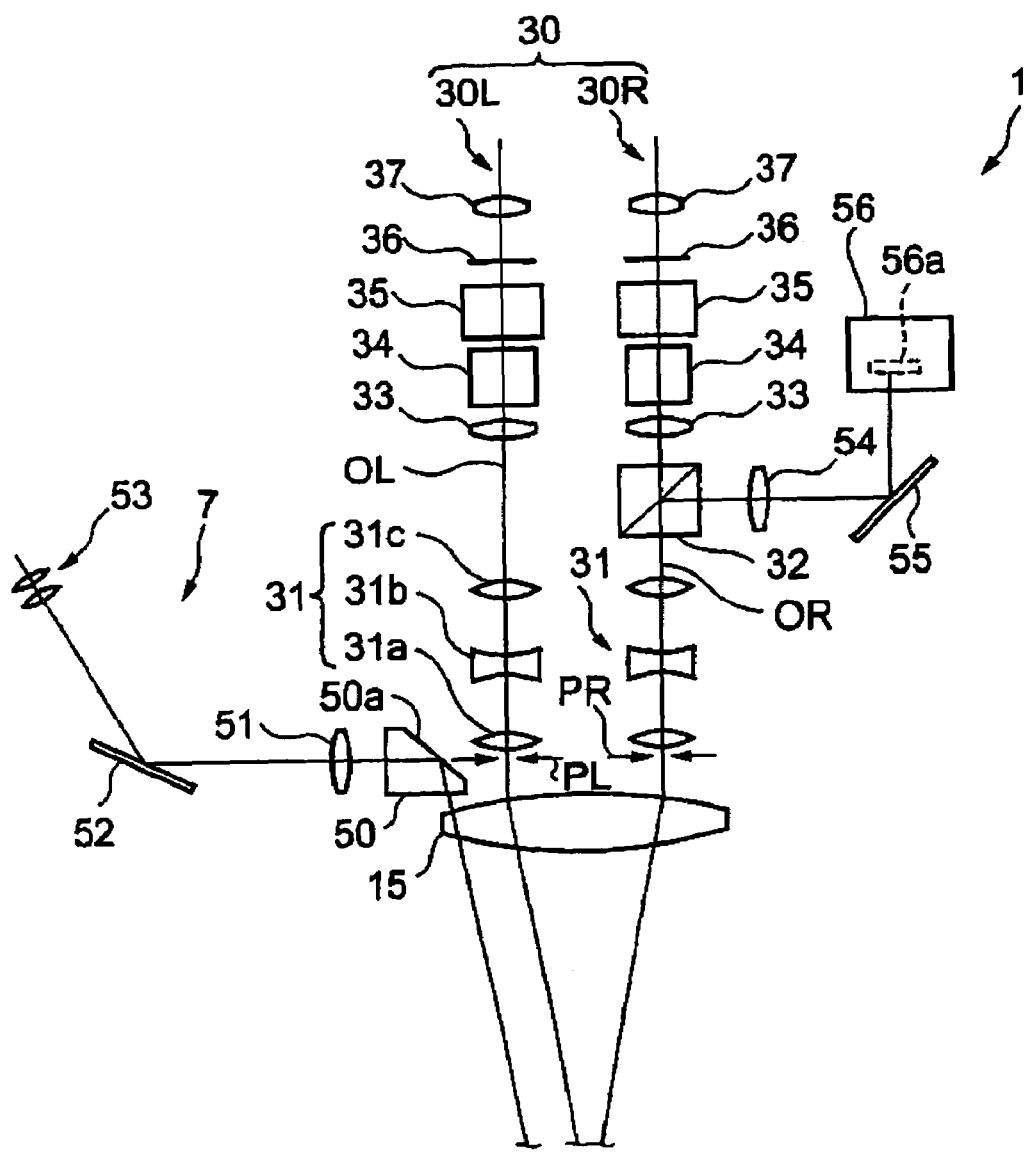
FIG. 6 is a schematic side view showing a structure of an optical system of the operation microscope apparatus according to the embodiment of the present invention.
Figure 15:
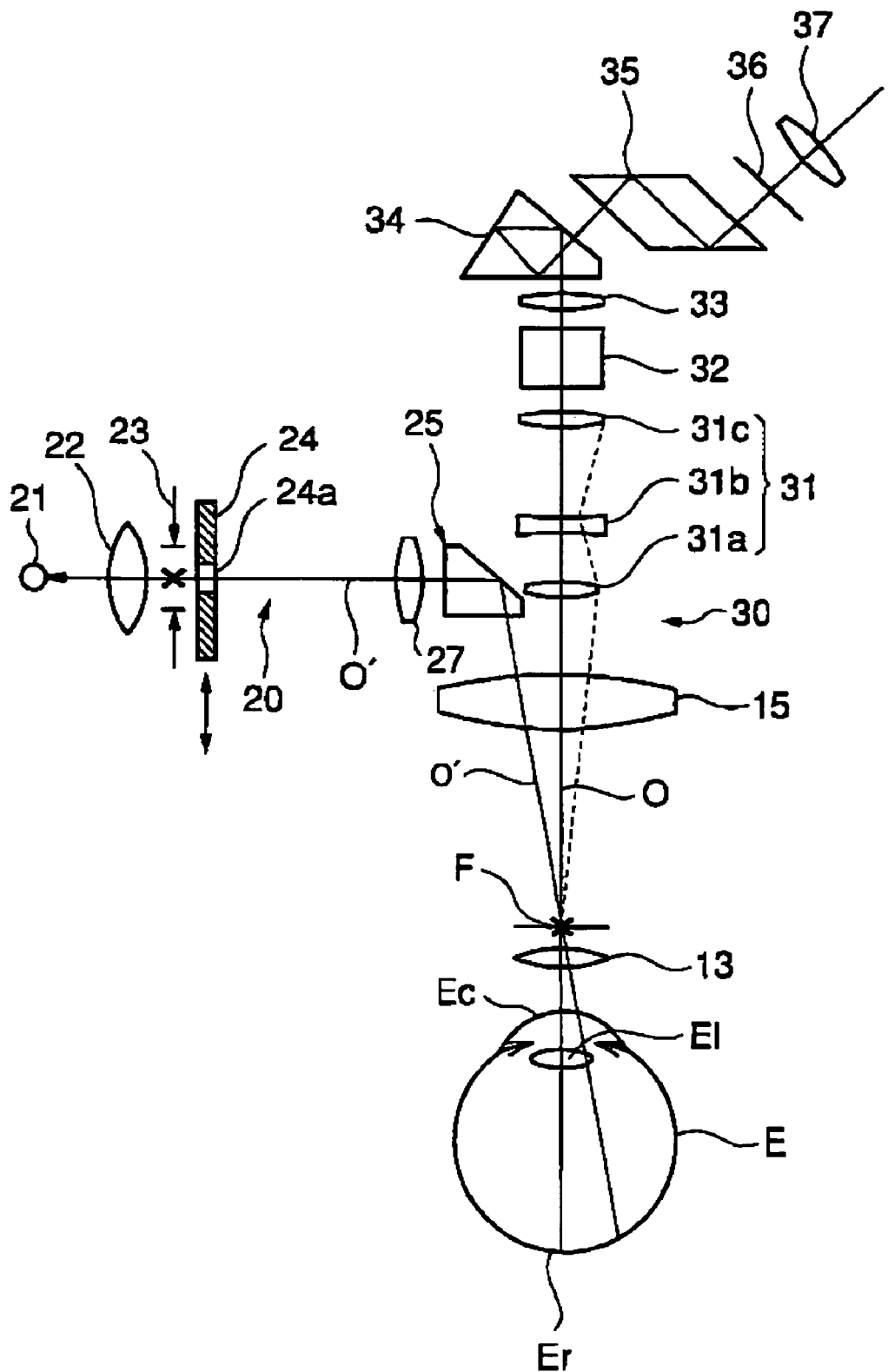
FIG. 15 is a schematic side view showing a structure of an optical system of the conventional operation microscope apparatus.

FIGS. 5 and 6 show structures of optical systems included in the operation microscope apparatus 1 according to this embodiment. FIG. 5 is a side view showing the optical systems as viewed from an assistant's microscope 7 side. FIG. 6 is a side view showing the optical systems as viewed from an operator side. The same symbols as those shown in FIG. 15 are used for the same constituent parts as those in the conventional operation microscope apparatus. Assume that longitudinal and lateral directions described below are directions as viewed from the operator side, unless otherwise specified.

[Observation Optical System]

As shown in FIG. 6, an observation optical system 30 includes a pair of left and right observation optical systems 30L and 30R which are provided on both sides of an optical axis O of the objective lens 15. Reference symbol OL denotes an observation optical axis of the left observation optical system 30L, and OR denotes an observation optical axis of the right observation optical system 30R. Each of the left and right observation optical systems 30L and 30R includes a zoom lens system 31, a beam splitter 32 (included in only the right observation optical system 30R), an imaging lens 33, an image erecting prism 34, an interpupillary distance adjusting prism 35, a field stop 36 and an eyepiece 37. The zoom lens system 31 is composed of a plurality of zoom lenses 31a, 31b and 31c.

The beam splitter 32 of the right observation optical system 30R is used to separate a part of observation light guided from the eye to be operated E along the observation optical axis OR from the other part thereof to lead the separated part to a TV camera image pickup system. The TV camera image pickup system includes an imaging lens 54, a reflecting mirror 55 and a TV camera 56. The TV camera 56 has an image pickup device 56a such as a CCD.

The assistant's microscope 7 includes optical systems disposed on right and left observation optical paths for assistant's right and left eyes, the right and left observation optical paths passing through the objective lens 15. As shown in FIG. 6, each of the optical systems of the assistant's microscope 7 includes an imaging lens 51 for imaging observation light from the eye to be operated E, the observation light being reflected on a reflective surface 50a of a prism 50 through the objective lens 15, a reflecting mirror 52 and an eyepiece 53. A specific zoom lens system (not shown) may be provided in the assistant's microscope 7. In this case, it is desirable to control a zoom magnification of an observation image obtained by the assistant's microscope 7 in association with a zoom magnification (for operator) of each of the zoom lens systems 31 of the observation optical system 30. An entrance pupil of each of the optical systems of the assistant's microscope 7 becomes the reflective surface 50a of the prism 50.

[Illumination Optical System]

As shown in FIG. 5, an illumination optical system 20 includes an illumination light source 21, an optical fiber 21a, a condenser lens 22, an illumination field stop 23, a slit plate 24, an illumination prism 25, an exit stop 26 and a collimator lens 27.

The illumination field stop 23 is provided in a position optically conjugate with a front focus position F of the objective lens 15. A slit hole 24a of the slit plate 24 is formed in a position substantially optically conjugate with the front focus position F. When the eye to be operated E is to be observed, a vertical position of the lens barrel section 10 of the operator's microscope 6 is adjusted such that the front focus position F of the objective lens 15 becomes conjugate with the fundus Er (retina) of the eye.

The illumination light source 21 according to this embodiment is provided outside the lens barrel section 10 of the operator's microscope 6. The illumination light source 21 is connected with one end of the optical fiber 21a. The other end of the optical fiber 21a is opposed to the condenser lens 22 of the lens barrel section 10. Illumination light from the illumination light source 21 is outputted from the other end of the optical fiber 21a and incident on the condenser lens 22. The illumination light source 21 and the optical fiber 21a correspond to an example of "output means" for outputting the illumination light in the present invention.

The exit stop 26 for shielding an arbitrary region of an exit is opposed to the other end (exit) of the optical fiber 21a. When the region of the exit which is shielded by the exit stop 26 is adjusted, an exit region of the illumination light changes. For example, when an upper side region of the exit is shielded by the exit stop 26, the illumination light is exited from only a lower side region of the exit and reflected on an upper side region of a reflective surface 25a of the illumination prism 25. On the other hand, when the lower side region of the exit is shielded, the illumination light is exited from only the upper side region of the exit and reflected on a lower side region of the reflective surface 25a of the illumination prism 25. Therefore, an illumination angle (for example, 7 degrees) obtained when the upper side region of the exit of the optical fiber 21a is shielded becomes larger than an illumination angle (for example, 4 degrees) obtained when the lower side region thereof is shielded. Here, the illumination angle indicates an angle (angle in lateral direction in FIG. 5) produced between the optical axes OL and OR of the observation optical system 30 (optical axis O of the objective lens 15) and the illumination optical axis O' of the illumination light incident on the eye to be operated E.

Figure 7:
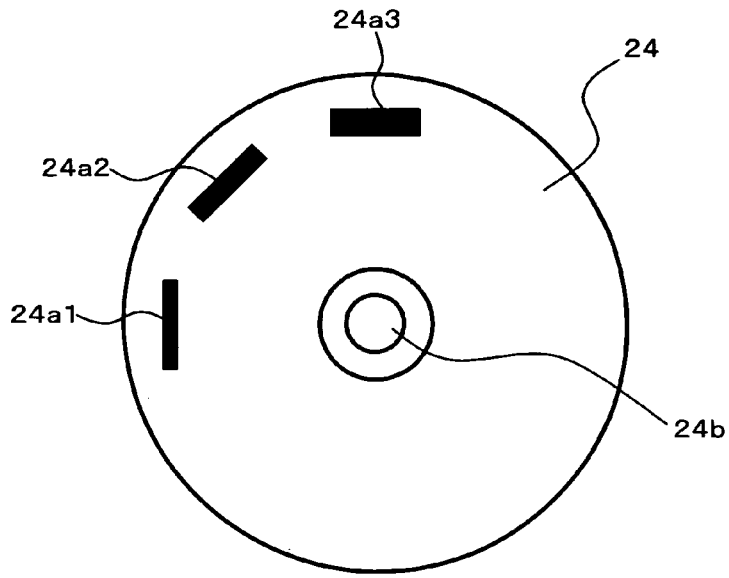
FIG. 7 is a schematic view showing a structure of a slit plate included in an illumination optical system of the operation microscope apparatus according to the embodiment of the present invention.

The slit plate 24 corresponds to an example of a "slit member" in the present invention. As shown in FIG. 7, the slit plate 24 is, for example, a disk-shaped light-shielding member including a plurality of (for example, three) rectangular slit holes 24a1, 24a2 and 24a3 formed therein. The plurality of slit holes formed in the slit plate 24 have different slit widths. In this embodiment, the slit widths of the three slit holes 24a1, 24a2 and 24a3 are set to 2.5 mm, 5 mm and 9 mm, respectively. The number of slit holes and the slit widths are not limited to the above-mentioned case and thus can be set as appropriate.

The slit plate 24 further includes a rotational shaft 24b provided in the central portion thereof. The rotational shaft 24b is connected with a slit plate rotating mechanism (described later) for rotating the slit plate 24. The slit holes 24a1, 24a2 and 24a3 are formed at the same distance from the center of rotation and selectively located on the illumination optical path of the illumination optical system 20 by the slit plate rotating mechanism. At this time, one of the slit holes 24a1, 24a2 and 24a3 located on the illumination optical path acts as the slit hole 24a shown in FIG. 5.

The slit plate 24 (and the slit plate rotating mechanism) is (are) moved in a direction orthogonal to the illumination optical axis O' of the illumination optical system 20 (in a direction indicated by a double-headed arrow "A" shown in FIG. 5) by a slit plate moving mechanism described later.

The collimator lens 27 converts the illumination light passing through the slit hole 24a into a parallel beam. The illumination light which is converted into the parallel beam is reflected on the reflective surface 25a of the illumination prism 25 and then incident on the objective lens 15. Then, the illumination light is emitted to the eye to be operated E through the front lens 13.

Figure 8:
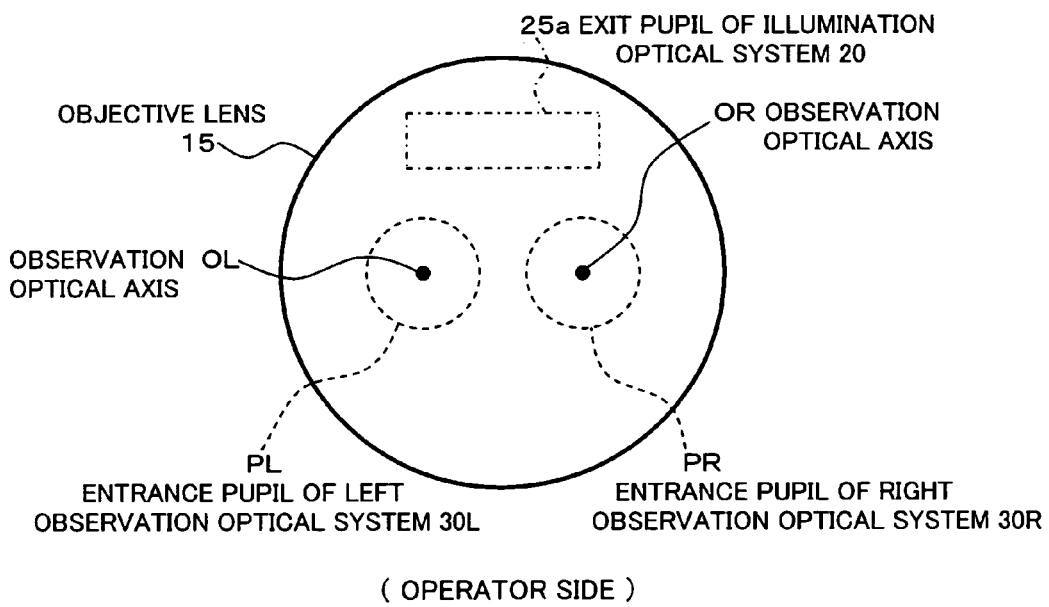
FIG. 8 is a schematic view showing a positional relationship between an exit pupil of the illumination optical system and entrance pupils of an observation optical system in the operation microscope apparatus according to the embodiment of the present invention.

FIG. 8 shows a positional relationship between an exit pupil of the illumination optical system 20 and an entrance pupil of the observation optical system 30 as viewed from above the observation optical system 30. The lower side of FIG. 8 is set as the operator side.

The exit pupil of the illumination optical system 20 is produced in the reflective surface 25a of the illumination prism 25. The exit pupil 25a of the illumination optical system 20 (the exit pupil 25a is identified with the reflective surface 25a) is produced in a position opposed to the operator across the observation optical systems 30L and 30R. The exit pupil 25a has a rectangular shape whose longitudinal direction is a direction joining the left and right observation optical axes OL and OR of the observation optical systems 30L and 30R with each other (lateral direction shown in FIG. 8). The slit plate 24 is disposed on the illumination optical path so as to align the longitudinal direction of the slit hole 24a with the longitudinal direction of the exit pupil 25a.

As shown in FIG. 6, an entrance pupil PL of the left observation optical system 30L is produced in a position between the objective lens 15 and the zoom lens system 31 of the left observation optical system 30L. An entrance pupil PR of right observation optical system 30R is produced in a position between the objective lens 15 and the zoom lens system 31 of the right observation optical system 30R. As shown in FIG. 8, the entrance pupils PL and PR of the left and right observation optical systems 30L and 30R are produced around the observation optical axes OL and OR, respectively.

[Structure of Control System]

Figure 9:
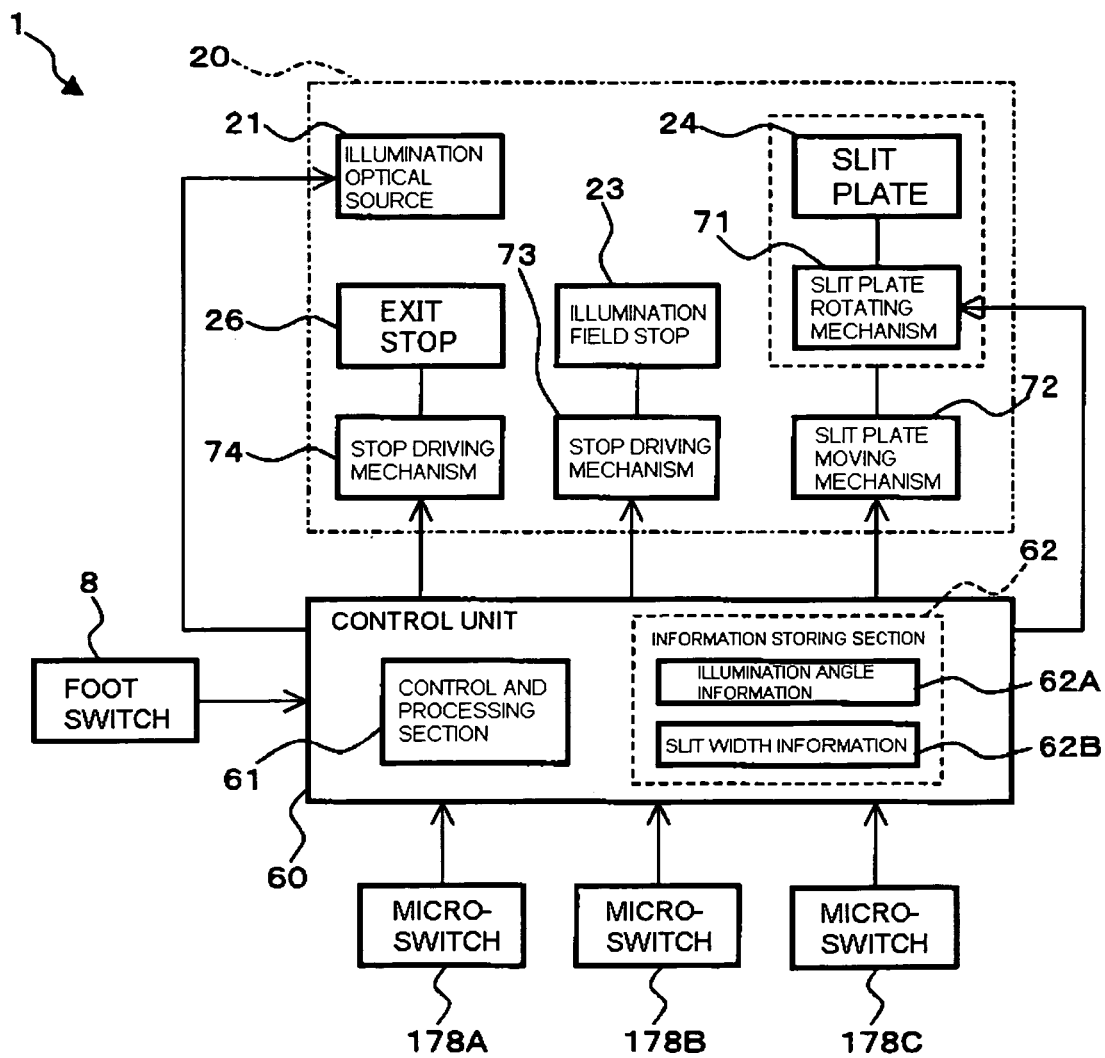
FIG. 9 is a block diagram showing a structure of a control system of the operation microscope apparatus according to the embodiment of the present invention.

Subsequently, a control system of the operation microscope apparatus 1 according to this embodiment will be described with reference to FIG. 9.

The control system of the operation microscope apparatus 1 includes a control unit 60 as a main part. The control unit 60 controls each apparatus part and includes a control and processing section 61 having a microprocessor such as a CPU, and an information storing section 62 having a storage device such as a RAM or a ROM. Computer programs for apparatus control (not shown) are stored in advance in the information storing section 62. The control and processing section 61 executes the computer programs to control each apparatus part. The control unit 60 corresponds to an example of "control means" in the present invention.

The information storing section 62 corresponds to "illumination angle information storing means" and "slit width information storing means" in the present invention and stores illumination angle information 62A and slit width information 62B in advance. The illumination angle information 62A and the slit width information 62B may be stored in the same storage device or separately stored in different storage devices.

The illumination angle information 62A is information for specifying the illumination angle of the illumination light which is associated with each of the plurality of front lenses 13A, 13B and 13C. For example, as shown in FIG. 10, the illumination angle information 62A is defined as information for specifying the illumination angle which is associated with the refractive power of each of the plurality of front lenses 13A, 13B and 13C. With respect to the illumination angle information 62A shown in FIG. 10, an illumination angle of 4 degrees is specified for the front lens 13A having the refractive power of 40 D. An illumination angle of 7 degrees is specified for the front lens 13B having the refractive power of 80 D. An illumination angle of 7 degrees is specified for the front lens 13C having the refractive power of 120 D. An illumination angle of 4 or 7 degrees is specified for the case where the front lens 13 is not located in the use position, such as the case where the front lens 13 is stored or the case where the front lens 13 is not attached. The illumination angle which can be specified is not limited to 4 or 7 degrees. The number of selectable illumination angles may be an arbitrary number equal to or larger than two.

The slit width information 62B is information for specifying the slit width of the slit hole 24a of the slit plate 24 which is associated with each of the plurality of front lenses 13A, 13B and 13C. For example, as shown in FIG. 11, the slit width information 62B is defined as information for specifying the slit width which is associated with the refractive power of each of the plurality of front lenses 13A, 13B and 13C. With respect to the slit width information 62B shown in FIG. 11, slit widths of 9 mm and 5 mm are specified for the front lens 13A having the refractive power of 40 D. Slit widths of 5 mm and 2.5 mm are specified for the front lens 13B having the refractive power of 80 D. A slit width of 2.5 mm is specified for the front lens 13C having the refractive power of 120 D. Slit widths of 9 mm, 5 mm and 2.5 mm are specified for the case where the front lens 13 is not located in the use position. The slit width which can be specified is not limited to 9 mm, 5 mm and 2.5 mm. The number of selectable slit widths may be an arbitrary number equal to or larger than two.

Figure 16A:
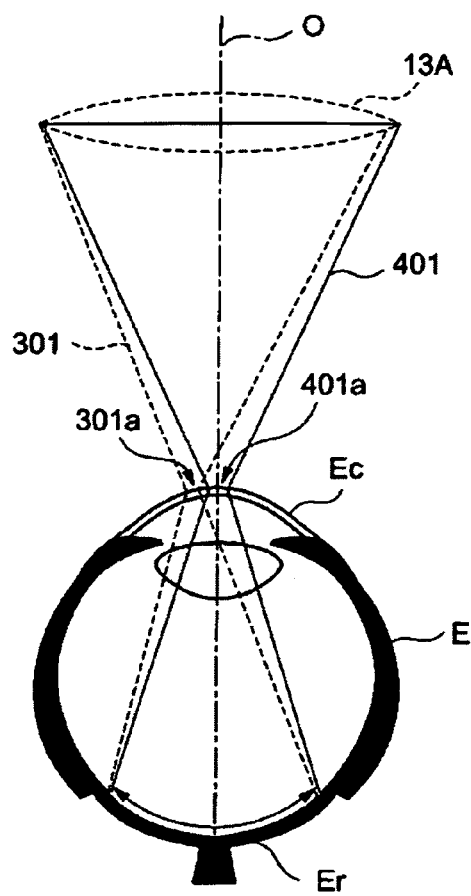
Figure 16B:
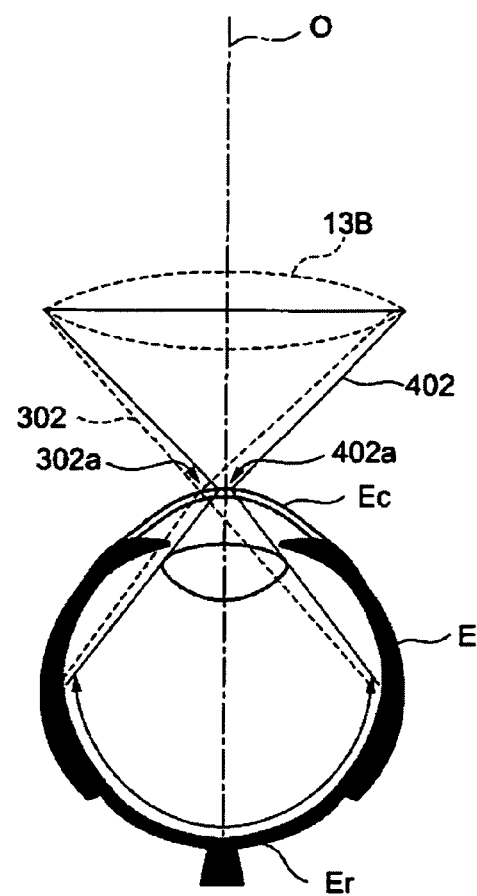
Figure 17A:
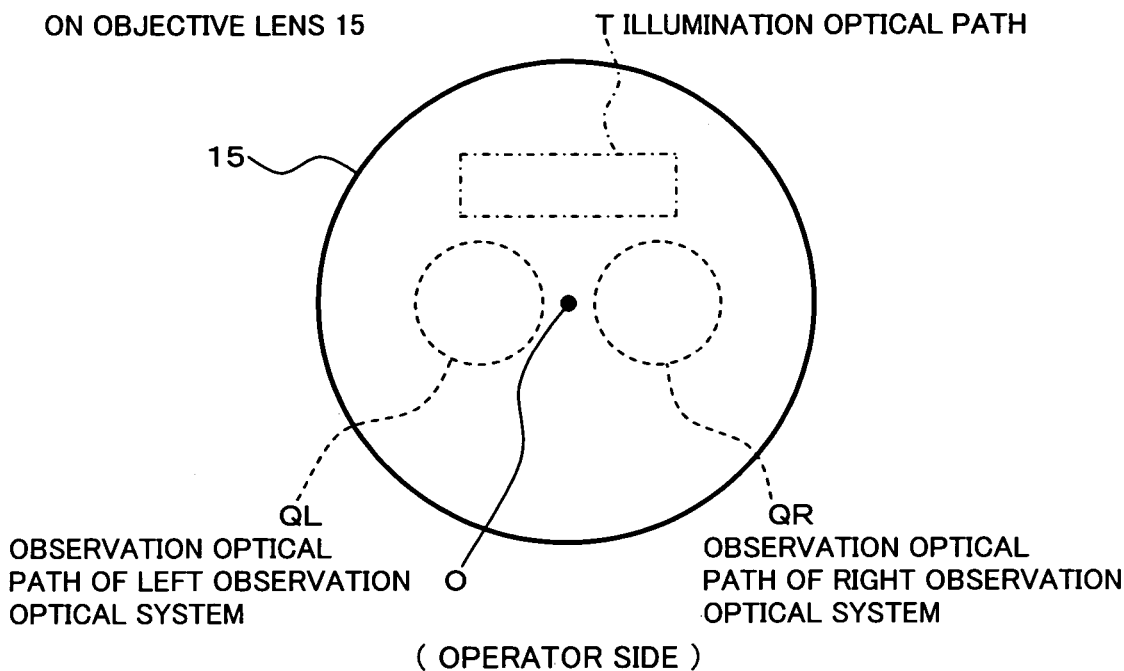
Figure 17B:
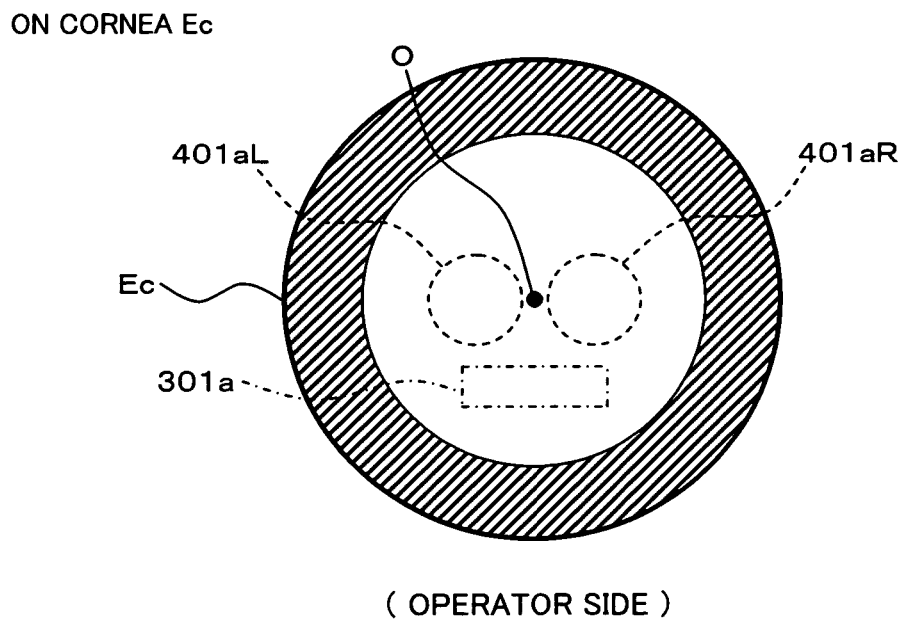
Figure 18A:
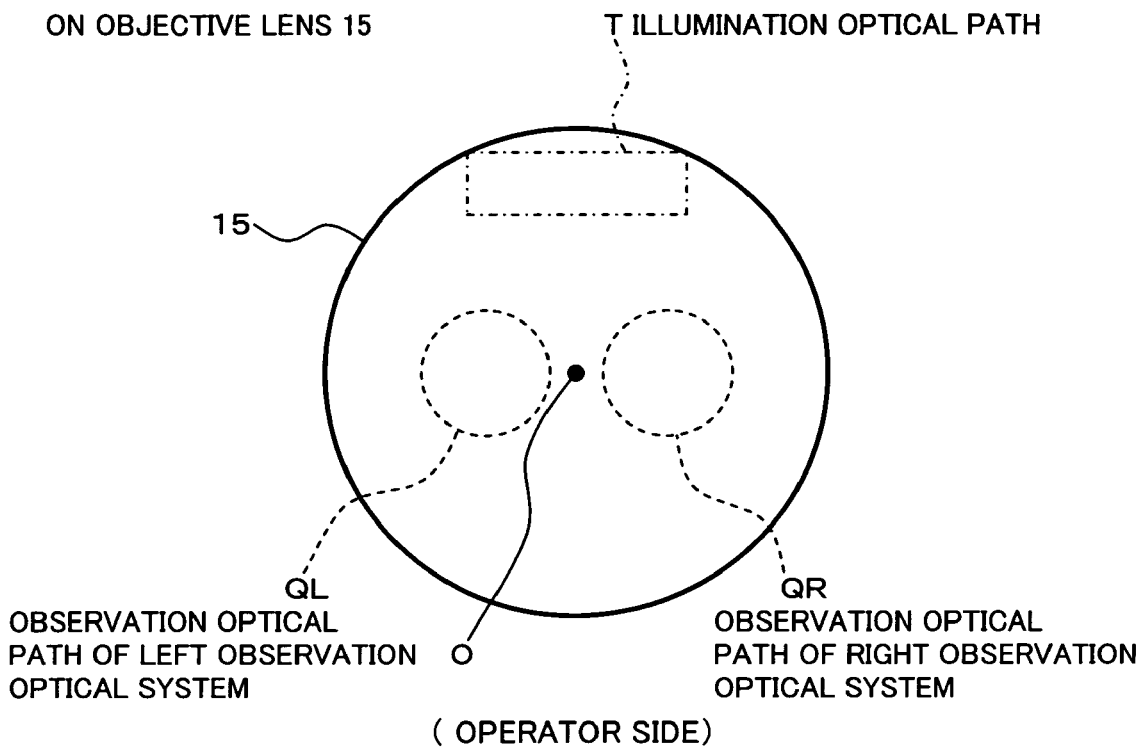
Figure 18B:
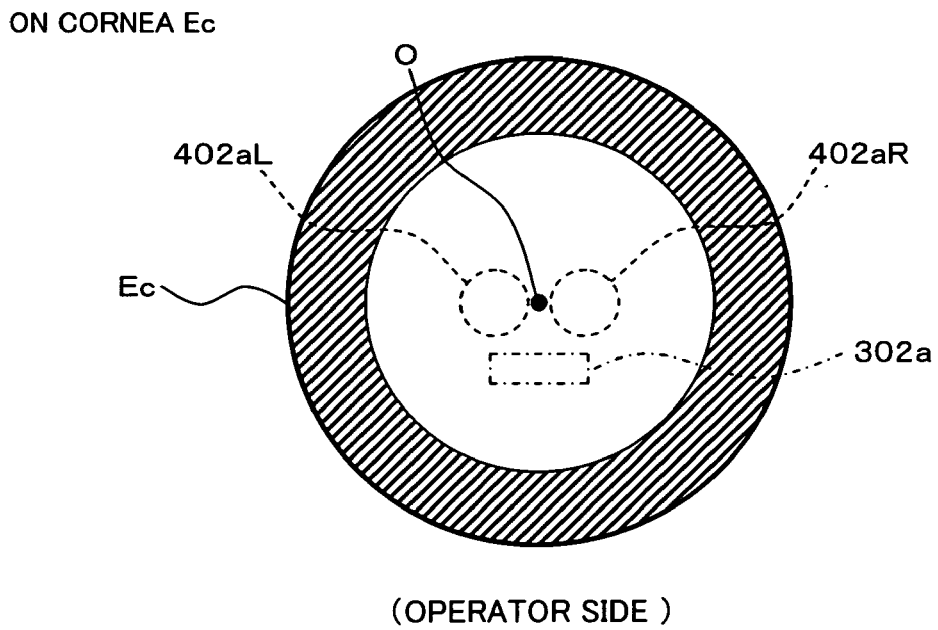

In order to ensure the suitable separation state between the illumination light and the observation light as shown in FIGS. 16A and 17B in the case where the front lens 13A having the refractive power of 40 D is used, it is desirable to set the illumination angle to approximately 4 degrees. In view of the amount of illumination light, it is desirable to set the slit width to approximately 9 mm to 5 mm. In order to ensure the suitable separation state between the illumination light and the observation light as shown in FIGS. 16B and 18B in the case where the front lens 13B having the refractive power of 80 D is used, it is desirable that the illumination angle be set to approximately 7 degrees and the slit width be set to approximately 5 mm to 2.5 mm. In order to ensure the suitable separation state in the case where the front lens 13C having the refractive power of 120 D is used, it is desirable that the illumination angle be set to approximately 7 degrees and the slit width be set to approximately 2.5 mm. That is, the illumination angle information 62A shown in FIG. 10 indicates a suitable illumination angle value in the case where each of the front lenses 13A, 13B and 13C is used. The slit width information 62B shown in FIG. 11 indicates a suitable slit width value in the case where each of the front lenses 13A, 13B and 13C is used.

As described above, the illumination optical system 20 includes the illumination light source 21, the illumination field stop 23, the slit plate 24 and the exit stop 26. The control unit 60 controls the illumination light source 21 to emit the illumination light or stop the emission thereof.

The slit plate 24 is driven by a slit plate rotating mechanism 71 and a slit plate moving mechanism 72 which are separately controlled. The slit plate rotating mechanism 71 includes a drive device such as a pulse motor and rotates the slit plate 24 about the rotational shaft 24b in response to a control signal sent from the control unit 60. The control unit 60 sends the control signal including a pulse signal with a predetermined number of pulses to the slit plate rotating mechanism 71. The slit plate rotating mechanism 71 rotates the slit plate 24 by an angle corresponding to the number of pulses of the pulse signal to selectively locate the slit holes 24a1, 24a2 and 24a3 on the illumination optical path. The slit plate rotating mechanism corresponds to an example of "drive means" in the present invention.

The slit plate moving mechanism 72 includes a drive device such as a pulse motor and operates to integrally move the slit plate 24 and the slit plate rotating mechanism 71 in response to a control signal sent from the control unit 60. A moving direction is the direction indicated by the double-headed arrow "A" shown in FIG. 5.

The illumination field stop 23 is driven by a stop driving mechanism 73 operated in response to a control signal sent from the control unit 60 to adjust an aperture value. The stop driving mechanism 73 has a known structure for adjusting an aperture value of a known stop member.

The exit stop 26 is driven by a known stop driving mechanism 74 operated in response to a control signal sent from the control unit 60 to shield an arbitrary region of the exit of the optical fiber 21a, thereby adjusting the illumination angle of the illumination light. The exit stop 26 and the stop driving mechanism 74 act to change an output position of the illumination light from the exit of the optical fiber 21a, and correspond to an example of "output position changing means" in the present invention.

As described above, each of the micro-switches 178A, 178B and 178C provided on the elevation regulating member 172 outputs the detection signal at a time when it is turned on. The detection signal is inputted to the control unit 60. As described above, the detection signals outputted from the micro-switches 178A, 178B and 178C have different voltage levels or the different numbers of pulses. The control unit 60 determines which one of the micro-switches 178A, 178B and 178C outputs the detection signal, based on the differences.

A manipulation signal from the foot switch 8 is inputted to the control unit 60. The foot switch 8 includes a manipulation section such as a button which is manipulated to adjust the illumination angle of the illumination light and a manipulation section such as a button which is manipulated to adjust the slit width of the slit hole 24a of the slit plate 24. The foot switch 8 corresponds to an example of "first manipulation means" and "second manipulation means" in the present invention.

[Operation Mode]

Figure 12:
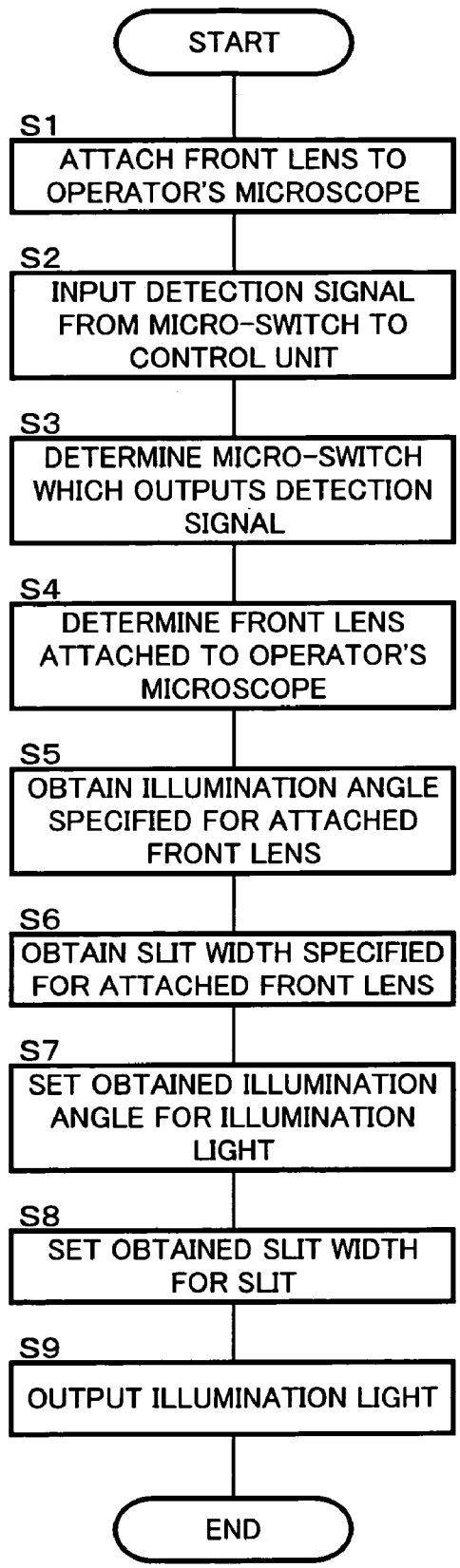
FIG. 12 is a flow chart showing an example of an operation mode of the operation microscope apparatus according to the embodiment of the present invention.
Figure 13:
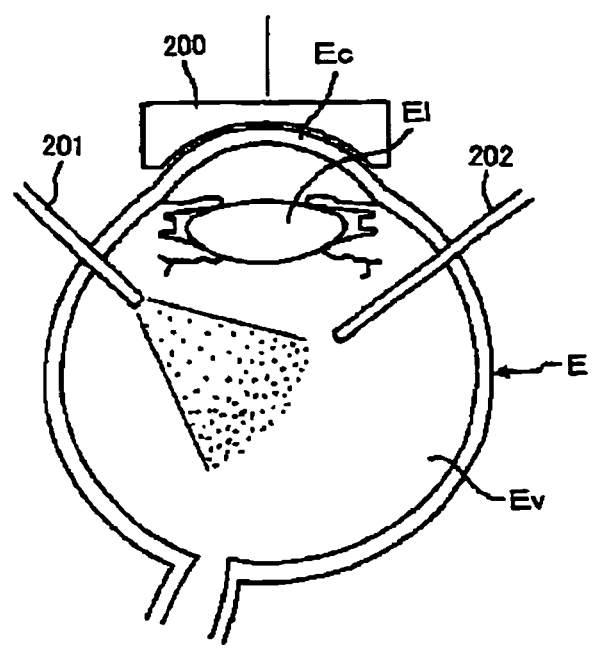
FIG. 13 is a cross sectional view showing a mode of an operation performed while a light guide is inserted into an interior of an eye to illuminate an observation region.

An operation mode of the operation microscope apparatus 1 having the above-mentioned structure according to this embodiment will be described. FIG. 12 is a flow chart showing an example of the operation mode of the operation microscope apparatus 1.

First, when the front lens 13A is to be attached to the operator's microscope 6, the operator or the like manually attaches the storing section 174 integrated with the front lens 13 to the elevation regulating member 172 (Step S1). At this time, the protruding portion 179 of the storing section 174 collides with the micro-switch 178 to input the detection signal from the micro-switch 178 in the control unit 60 (Step S2).

The control and processing section 61 determines which one of the micro-switches 178A, 178B and 178C outputs the detection signal, based on, for example, the voltage level and the number of pulses which are included in the inputted detection signal (Step S3). Then, control and processing section 61 determines which one of the front lenses 13A, 13B and 13C is attached to the operator's microscope 6, based on the determined micro-switch 178 (Step S4).

After that, the control and processing section 61 consults the illumination angle information 62A stored in the information storing section 62 and obtains the illumination angle of the illumination light which is specified for the determined one of the front lenses 13A, 13B and 13C (Step S5). Then, the control and processing section 61 consults the slit width information 62B and obtains the slit width of the slit hole 24a of the slit plate 24 which is specified for the determined one of the front lenses 13A, 13B and 13C (Step S6).

Subsequently, the control and processing section 61 controls the stop driving mechanism 74 to drive the exit stop 26 to set the illumination angle of the illumination light to the illumination angle obtained in Step S5 (Step S7). Then, the control and processing section 61 controls the slit plate rotating mechanism 71 to rotate the slit plate 24, thereby locating the slit hole 24a having the slit width obtained in Step S6 on the illumination optical axis O' (Step S8).

When a plurality of illumination angle values are obtained in Step S5, predetermined one of the plurality of specified values is set in Step S7. When a plurality of slit widths are obtained in Step S6, predetermined one of the plurality of specified values is set in Step S8. The operator can manipulate the foot switch 8 to adjust the set values as appropriate.

The control and processing section 61 controls the illumination light source 21 in response to the request of the operator or the like (for example, manipulation of the foot switch 8) to output the illumination light from the exit of the optical fiber 21a (Step S9). Then, the operation at the time of attachment of the front lens 13 is completed. Therefore, the operation microscope apparatus 1 becomes a state in which the eye to be operated E can be observed.

Specific Example of Operation

A specific example of the operation mode described above will be described. For example, when the front lens 13B whose refractive power is 80 D is attached (Step S1), the protruding portion 179B of the storing section 174B integrated with the front lens 13B collides with the micro-switch 178B to input the detection signal from the micro-switch 178B in the control unit 60 (Step S2).

The control and processing section 61 determines the micro-switch 178B which has outputted the detection signal, based on the inputted detection signal (Step S3) and determines the attached front lens 13B (Step S4).

After that, the illumination angle information 62A is consulted to obtain the illumination angle of "7 degrees" which is specified for the front lenses 13B (Step S5). Then, the slit width information 62B is consulted to obtain the slit widths of "5 mm, 2.5 mm" which are specified for the front lens 13B (Step S6).

Subsequently, the stop driving mechanism 74 is controlled such that the exit stop 26 shields the upper region of the exit of the optical fiber 21a to set the illumination angle of the illumination light to 7 degrees (Step S7). Then, the slit plate rotating mechanism 71 is controlled such that the slit plate 24 is rotated to locate the slit hole 24a2 having the slit width of 5 mm which is predetermined one of the specified slit widths of "5 mm, 2.5 mm", on the illumination optical axis O' (Step S8). If necessary, the operator can manipulate the foot switch 8 to change the slit width to 2.5 mm. The illumination light source 21 is driven in response to the request of the operator to output the illumination light from the exit of the optical fiber 21a (Step S9).

The operation microscope apparatus 1 according to this embodiment has a structure capable of manually adjusting the illumination angle and the slit width in addition to the above-mentioned structure capable of automatically adjusting the illumination angle and the slit width. Although a control system is not shown, when the switch 167 of the lens barrel section 10 of the operator's microscope 6 is manipulated to select one of the front lenses 13A, 13B and 13C which is attached, a manipulation signal (identification information) outputted from the switch 167 is inputted in the control unit 60. The control unit 60 determines that which front lens 13 is attached, based on the manipulation signal and consults the illumination angle information 62A and the slit width information 62B to obtain the illumination angle and the slit width which are specified for the determined front lens 13. Then, the stop driving mechanism 74 and the slit plate rotating mechanism 71 are controlled to set the obtained illumination angle and the obtained slit width.

[Operation and Effect]

According to the above-mentioned operation microscope apparatus 1 in this embodiment, when any of the front lenses 13A, 13B and 13C is attached, the detection signal for identifying the attached front lens 13 (identification information) is inputted in the control unit 60. The control unit 60 performs the control for emitting the illumination light at the illumination angle corresponding to the detection signal and the control for locating a slit having the slit width corresponding to the detection signal on the illumination optical path. Therefore, once the front lens is attached, the illumination angle of the illumination light and the slit width of the slit are automatically adjusted. Thus, it is possible to easily and speedily ensure the suitable separation state between the illumination light and the observation light.

A plurality of slit widths such as the slit widths corresponding to the front lens 13A whose refractive power is 40 D or the front lens 13B whose refractive power is 80 D, the slit widths being included in the slit width information 62B (see FIG. 11), are set for the single front lens 13. A structure capable of switching between the plurality of slit widths by the foot switch 8 or the like is employed. Therefore, the observation can be performed in view of the separation state between the illumination light and the observation light and the amount of illumination light.

As in the case of the slit width, a structure capable of switching between a plurality of illumination angles can be employed. For example, it is possible that both 4 degrees and 7 degrees be specified as the illumination angles corresponding to the front lens 13A whose refractive power is 40 D and the illumination angles be switched therebetween by the foot switch 8 or the like.

According to the above-mentioned operation microscope apparatus 1 in this embodiment, it is possible to select the front lens to be used by the switch 167. According to such manual input, once the front lens to be used is selected, the illumination angle and the slit width which are suitable to use the front lens are automatically set. Therefore, the suitable separation state between the illumination light and the observation light can be easily and speedily ensured.

MODIFIED EXAMPLE

The structure described above in detail is merely an example of a structure for suitably implementing the operation microscope apparatus according to the present invention. Therefore, arbitrary modifications can be made without departing from the gist of the present invention. Hereinafter, such a modified example will be described.

In the above-mentioned embodiment, the switches 167 are provided on the lens barrel section 10 of the operator's microscope 6 to manually specify the front lens 13 to be used. Input means for specifying the front lens, such as a switch or a button, may be provided on another portion of the operation microscope apparatus 1, such as on the foot switch 8.

In the above-mentioned embodiment, both the illumination angle and the slit width are automatically set based on the inputted identification information. Only one of the illumination angle and the slit width may be automatically set.

When the present invention is applied to an operation microscope apparatus including a plurality of illumination optical systems with different illumination directions as described in Japanese Patent Application No. 2005-107951 made by the applicant of the present invention, illumination angles and/or slit widths for the respective illumination optical systems can be simultaneously set.

In the above-mentioned embodiment, the input means (detection means) such as each of the micro-switches 178 is provided for the storing section 174 integrated with the front lens 13. However, a position in which the input means is provided is arbitrary. For example, when only the front lens is replaced by another one, it is possible to employ a structure in which input instruction means for determining attachment directions of respective front lenses, such as protruding portions, are provided in different positions of the circumferences of the front lenses and detection means such as microsensors are provided in positions corresponding to the respective protruding portions, of an inner circumference of the holding plate 141a. When a structure in which a holder (holding plate 141a in the above-mentioned embodiment) for holding the front lens 13 is replaced by another one is employed, the input means (detection means) can be provided in a connection portion between the holder and the arm section 141.

The input means in the present invention is not limited to the micro-switch in the above-mentioned embodiment. It is possible to employ an arbitrary structure in which the input means has a function for inputting, to the control unit, identification information for identifying, of a plurality of front lenses which are selectively used, a front lens located in the used position, that is, a front lens which becomes a state which can be transferred to the use state.

In an example of this input means, when an image taken by the TV camera 56 is analyzed, the used front lens can be determined. In order to realize this, for example, identification information is provided to the holding plate 141a for each front lens 13. Arbitrary information capable of identifying a plurality of front lenses, such as a bar code, a mark including a line, or color information can be used as the identification information. The identification information can be provided on, for example, an upper surface of a region of the holding plate 141a, which surrounds the front lens 13 or an upper surface of an arm portion extended from the region to a connection position with the arm section 141.

The TV camera 56 takes an image including the identification information of the front lens 13 located in the use position. At this time, if necessary, an image taking magnification of the zoom lens system 31 is reduced to include the identification information within an image taking area. The taken image (data) including the identification information is inputted from the TV camera 56 in the control unit 60. The control unit 60 analyzes the inputted image to identify the identification information provided to the holding plate 141a or the like and determines which front lens 13 is located in the use position. The illumination angle and the slit width are automatically set based on a result obtained by the determination. Here, the "input means" in the present invention includes the TV camera 56.

In another example using the TV camera 56, it is possible to employ a method of taking a reflection image of the exit pupil 25a of the illumination optical system 20 on a lens surface (lens surface located on the objective lens 15 side and/or the side of the eye to be operated E) of the front lens 13 located in the use position and analyzing the taken reflection image to determine the front lens 13. The reflection image of the exit pupil 25a on the lens surface of the front lens 13 is formed in the same rectangular shape as that of each of projection images of the exit pupil 25a on the objective lens 15 and the cornea Ec as shown in FIGS. 17A, 17B, 18A and 18B. A reflection image whose size, position, and distortion are changed according to a curved shape (curvature) of the lens surface of the front lens 13 is taken. When the respective front lenses are made of the same lens material, the curvature of the lens surface of the front lens becomes larger as the refractive power thereof increases.

Here, information including a size, a position, and a distortion (which is referred to as reflection image information) of the reflection image of the exit pupil 25a (for example, in the case where each of the illumination angle and the image taking magnification is a predetermined value) are obtained in advance for each front lens 13 by measurement or calculation. Then, at the time of operation, when the front lens 13 is located in the use position and illumination light is emitted, the reflection image of the exit pupil 25a resulting from the emitted illumination light is taken by the TV camera 56. The taken image is inputted as the "identification information" in the present invention from the TV camera 56 in the control unit 60.

The control unit 60 analyses the taken image and obtains the size, the position, and the distortion of the reflection image of the exit pupil 25a. The control unit 60 determines the front lens 13 corresponding to the obtained size and the like based on the reflection image information. The illumination angle and the slit width are set based on a result obtained by the determination.

What is claimed is:

1. An operation microscope apparatus, comprising:
   an illumination optical system for emitting illumination light to an eye to be operated at a predetermined illumination angle;
   an objective lens;
   a front lens for condensing the illumination light from the illumination optical system to illuminate an interior of the eye to be operated, the front lens being provided in a use position between the eye to be operated and a front focus point of the objective lens in which a plurality of front lenses having different refractive powers are selectively located;
   an observation optical system including an eyepiece, for guiding, to the eyepiece, reflection light of the illumination light from the eye to be operated through the front lens and the objective lens;
   input means for inputting identification information for identifying the front lens located in the use position, of the plurality of front lenses; and
   control means for controlling the illumination optical system to set an illumination angle of the illumination light to an illumination angle corresponding to the inputted identification information.

2. An operation microscope apparatus according to claim 1, wherein:
   the control means comprises illumination angle information storing means for storing illumination angle information for specifying illumination angles of the illumination light which correspond to the plurality of front lenses; and
   the control means obtains an illumination angle specified for the front lens identified by the inputted identification information based on the illumination angle information and sets the illumination angle of the illumination light to the obtained illumination angle.

3. An operation microscope apparatus according to claim 2, further comprising a first manipulation means for adjusting the illumination angle of the illumination light,
wherein the control means specifies a plurality of illumination angles corresponding to the identification information inputted by the input means and controls the illumination optical system in response to a manipulation signal from the first manipulation means to selectively set the plurality of specified illumination angles for the illumination light.

4. An operation microscope apparatus according to claim 3, wherein:
each of the plurality of front lenses and a member integrated with each of the plurality of front lenses comprises input instruction means for instructing an input of the identification information which is provided therein; and
the input means comprises detecting means for detecting an instruction from the input instruction means and outputs the identification information corresponding to a result obtained by the detection means to the control means.

5. An operation microscope apparatus according to claim 2, wherein:
the illumination optical system further comprises output means for outputting the illumination light and output position changing means for changing an output position of the illumination light from the output means; and
the control means controls the output position adjusting means to adjust the illumination angle of the illumination light by changing the output position of the illumination light.

6. An operation microscope apparatus according to claim 5, further comprising a first manipulation means for adjusting the illumination angle of the illumination light,
wherein the control means specifies a plurality of illumination angles corresponding to the identification information inputted by the input means and controls the illumination optical system in response to a manipulation signal from the first manipulation means to selectively set the plurality of specified illumination angles for the illumination light.

7. An operation microscope apparatus according to claim 6, wherein:
each of the plurality of front lenses and a member integrated with each of the plurality of front lenses comprises input instruction means for instructing an input of the identification information which is provided therein; and
the input means comprises detecting means for detecting an instruction from the input instruction means and outputs the identification information corresponding to a result obtained by the detection means to the control means.

8. An operation microscope apparatus according to claim 1, wherein:
the illumination optical system further comprises output means for outputting the illumination light and output position changing means for changing an output position of the illumination light from the output means; and
the control means controls the output position adjusting means to adjust the illumination angle of the illumination light by changing the output position of the illumination light.

9. An operation microscope apparatus according to claim 1, further comprising a first manipulation means for adjusting the illumination angle of the illumination light,
wherein the control means specifies a plurality of illumination angles corresponding to the identification information inputted by the input means and controls the illumination optical system in response to a manipulation signal from the first manipulation means to selectively set the plurality of specified illumination angles for the illumination light.

10. An operation microscope apparatus according to claim 1, wherein:
each of the plurality of front lenses and a member integrated with each of the plurality of front lenses comprises input instruction means for instructing an input of the identification information which is provided therein; and
the input means comprises detecting means for detecting an instruction from the input instruction means and outputs the identification information corresponding to a result obtained by the detection means to the control means.

11. An operation microscope apparatus, comprising:
an illumination optical system for emitting illumination light to an eye to be operated at a predetermined illumination angle, the illumination optical system including slit means for adjusting a slit width of a slit for transmitting a part of the illumination light, the slit being formed in the slit means;
an objective lens;
a front lens for condensing the illumination light from the illumination optical system to illuminate an interior of the eye to be operated, the front lens being provided in a use position between the eye to be operated and a front focus point of the objective lens in which a plurality of front lenses having different refractive powers are selectively located;
an observation optical system including an eyepiece, for guiding, to the eyepiece, reflection light of the illumination light from the eye to be operated through the front lens and the objective lens;
input means for inputting identification information for identifying the front lens located in the use position, of the plurality of front lenses; and
control means for controlling the slit means to set the slit width of the slit to a slit width corresponding to the inputted identification information.

12. An operation microscope apparatus according to claim 11, wherein:
the control means comprises illumination angle information storing means for storing illumination angle information for specifying illumination angles of the illumination light which correspond to the plurality of front lenses; and
the control means obtains an illumination angle specified for the front lens identified by the inputted identification information based on the illumination angle information and sets the illumination angle of the illumination light to the obtained illumination angle.

13. An operation microscope apparatus according to claim 12, further comprising a first manipulation means for adjusting the illumination angle of the illumination light,
wherein the control means specifies a plurality of illumination angles corresponding to the identification information inputted by the input means and controls the illumination optical system in response to a manipulation signal from the first manipulation means to selectively set the plurality of specified illumination angles for the illumination light.

14. An operation microscope apparatus according to claim 13, wherein:

the each of the plurality of front lenses and a member integrated with each of the plurality of front lenses comprises input instruction means for instructing an input of the identification information which is provided therein; and the input means comprises detecting means for detecting an instruction from the input instruction means and outputs the identification information corresponding to a result obtained by the detection means to the control means.

15. An operation microscope apparatus according to claim 12, wherein:

the illumination optical system further comprises output means for outputting the illumination light and output position changing means for changing an output position of the illumination light from the output means; and the control means controls the output position adjusting means to adjust the illumination angle of the illumination light by changing the output position of the illumination light.

16. An operation microscope apparatus according to claim 15, further comprising a first manipulation means for adjusting the illumination angle of the illumination light, wherein the control means specifies a plurality of illumination angles corresponding to the identification information inputted by the input means and controls the illumination optical system in response to a manipulation signal from the first manipulation means to selectively set the plurality of specified illumination angles for the illumination light.

17. An operation microscope apparatus according to claim 16, wherein:

each of the plurality of front lenses and a member integrated with each of the plurality of front lenses comprises input instruction means for instructing an input of the identification information which is provided therein; and the input means comprises detecting means for detecting an instruction from the input instruction means and outputs the identification information corresponding to a result obtained by the detection means to the control means.

18. An operation microscope apparatus according to claim 11, wherein:

the control means comprises slit width information storing means for storing slit width information for specifying slit widths corresponding to the plurality of front lenses; and the control means obtains a slit width specified for the front lens identified by the inputted identification information based on the slit width information and sets the slit width of the slit means to the obtained slit width.

19. An operation microscope apparatus according to claim 18, further comprising a second manipulation means for adjusting the slit width of the slit, wherein the control means specifies a plurality of slit widths corresponding to the identification information inputted by the input means and controls the slit means in response to a manipulation signal from the second manipulation means to selectively set the plurality of specified slit widths for the slit.

20. An operation microscope apparatus according to claim 19, wherein:

each of the plurality of front lenses and a member integrated with each of the plurality of front lenses comprises input instruction means for instructing an input of the identification information which is provided therein; and the input means comprises detecting means for detecting an instruction from the input instruction means and outputs the identification information corresponding to a result obtained by the detection means to the control means.

21. An operation microscope apparatus according to claim 18, wherein:

the slit means comprises a slit member including a plurality of slit hole portions having different slit widths which are formed therein and drive means for driving the slit member to locate one of the plurality of slit hole portions on an optical path of the illumination light; and the control means controls the drive means to adjust the slit width by changing the one of the plurality of slit hole portions, which is located on the optical path, to another one.

22. An operation microscope apparatus according to claim 21, further comprising a second manipulation means for adjusting the slit width of the slit, wherein the control means specifies a plurality of slit widths corresponding to the identification information inputted by the input means and controls the slit means in response to a manipulation signal from the second manipulation means to selectively set the plurality of specified slit widths for the slit.

23. An operation microscope apparatus according to claim 22, wherein:

each of the plurality of front lenses and a member integrated with each of the plurality of front lenses comprises input instruction means for instructing an input of the identification information which is provided therein; and the input means comprises detecting means for detecting an instruction from the input instruction means and outputs the identification information corresponding to a result obtained by the detection means to the control means.

24. An operation microscope apparatus according to claim 11, wherein:

the slit means comprises a slit member including a plurality of slit hole portions having different slit widths which are formed therein and drive means for driving the slit member to locate one of the plurality of slit hole portions on an optical path of the illumination light; and the control means controls the drive means to adjust the slit width by changing the one of the plurality of slit hole portions, which is located on the optical path, to another one.

25. An operation microscope apparatus according to claim 11, further comprising a second manipulation means for adjusting the slit width of the slit, wherein the control means specifies a plurality of slit widths corresponding to the identification information inputted by the input means and controls the slit means in response to a manipulation signal from the second manipulation means to selectively set the plurality of specified slit widths for the slit.

26. An operation microscope apparatus according to claim 11, wherein:

each of the plurality of front lenses and a member integrated with each of the plurality of front lenses comprises input instruction means for instructing an input of the identification information which is provided therein; and the input means comprises detecting means for detecting an instruction from the input instruction means and outputs the identification information corresponding to a result obtained by the detection means to the control means.

27. An operation microscope apparatus, comprising:
an illumination optical system for emitting illumination light to an eye to be operated at a predetermined illumination angle, the illumination optical system including slit means for adjusting a slit width of a slit for transmitting a part of the illumination light, the slit being formed in the slit means;
an objective lens;
a front lens for condensing the illumination light from the illumination optical system to illuminate an interior of the eye to be operated, the front lens being provided in a use position between the eye to be operated and a front focus point of the objective lens in which a plurality of front lenses having different refractive powers are selectively located;
an observation optical system including an eyepiece, for guiding, to the eyepiece, reflection light of the illumination light from the eye to be operated through the front lens and the objective lens;
input means for inputting identification information for identifying the front lens located in the use position, of the plurality of front lenses; and
control means for controlling the illumination optical system to set an illumination angle of the illumination light to an illumination angle corresponding to the inputted identification information and controlling the slit means to set the slit width of the slit to a slit width corresponding to the inputted identification information.

28. An operation microscope apparatus according to claim 27, wherein:
the control means comprises illumination angle information storing means for storing illumination angle information for specifying illumination angles of the illumination light which correspond to the plurality of front lenses; and
the control means obtains an illumination angle specified for the front lens identified by the inputted identification information based on the illumination angle information and sets the illumination angle of the illumination light to the obtained illumination angle.

29. An operation microscope apparatus according to claim 28, further comprising a first manipulation means for adjusting the illumination angle of the illumination light,
wherein the control means specifies a plurality of illumination angles corresponding to the identification information inputted by the input means and controls the illumination optical system in response to a manipulation signal from the first manipulation means to selectively set the plurality of specified illumination angles for the illumination light.

30. An operation microscope apparatus according to claim 29, wherein:
each of the plurality of front lenses and a member integrated with each of the plurality of front lenses comprises input instruction means for instructing an input of the identification information which is provided therein; and
the input means comprises detecting means for detecting an instruction from the input instruction means and outputs the identification information corresponding to a result obtained by the detection means to the control means.

31. An operation microscope apparatus according to claim 28, wherein:
the illumination optical system further comprises output means for outputting the illumination light and output position changing means for changing an output position of the illumination light from the output means; and
the control means controls the output position adjusting means to adjust the illumination angle of the illumination light by changing the output position of the illumination light.

32. An operation microscope apparatus according to claim 31, further comprising a first manipulation means for adjusting the illumination angle of the illumination light,
wherein the control means specifies a plurality of illumination angles corresponding to the identification information inputted by the input means and controls the illumination optical system in response to a manipulation signal from the first manipulation means to selectively set the plurality of specified illumination angles for the illumination light.

33. An operation microscope apparatus according to claim 32, wherein:
each of the plurality of front lenses and a member integrated with each of the plurality of front lenses comprises input instruction means for instructing an input of the identification information which is provided therein; and
the input means comprises detecting means for detecting an instruction from the input instruction means and outputs the identification information corresponding to a result obtained by the detection means to the control means.

34. An operation microscope apparatus according to claim 27, wherein:
the control means comprises slit width information storing means for storing slit width information for specifying slit widths corresponding to the plurality of front lenses; and
the control means obtains a slit width specified for the front lens identified by the inputted identification information based on the slit width information and sets the slit width of the slit means to the obtained slit width.

35. An operation microscope apparatus according to claim 34, further comprising a second manipulation means for adjusting the slit width of the slit,
wherein the control means specifies a plurality of slit widths corresponding to the identification information inputted by the input means and controls the slit means in response to a manipulation signal from the second manipulation means to selectively set the plurality of specified slit widths for the slit.

36. An operation microscope apparatus according to claim 35, wherein:
each of the plurality of front lenses and a member integrated with each of the plurality of front lenses comprises input instruction means for instructing an input of the identification information which is provided therein; and
the input means comprises detecting means for detecting an instruction from the input instruction means and outputs the identification information corresponding to a result obtained by the detection means to the control means.

37. An operation microscope apparatus according to claim 34, wherein:

the slit means comprises a slit member including a plurality of slit hole portions having different slit widths which are formed therein and drive means for driving the slit member to locate one of the plurality of slit hole portions on an optical path of the illumination light; and the control means controls the drive means to adjust the slit width by changing the one of the plurality of slit hole portions, which is located on the optical path, to another one.

38. An operation microscope apparatus according to claim 37, further comprising a second manipulation means for adjusting the slit width of the slit, wherein the control means specifies a plurality of slit widths corresponding to the identification information inputted by the input means and controls the slit means in response to a manipulation signal from the second manipulation means to selectively set the plurality of specified slit widths for the slit.

39. An operation microscope apparatus according to claim 38, wherein:

each of the plurality of front lenses and a member integrated with each of the plurality of front lenses comprises input instruction means for instructing an input of the identification information which is provided therein; and the input means comprises detecting means for detecting an instruction from the input instruction means and outputs the identification information corresponding to a result obtained by the detection means to the control means.

40. An operation microscope apparatus according to claim 27, wherein:

the illumination optical system further comprises output means for outputting the illumination light and output position changing means for changing an output position of the illumination light from the output means; and the control means controls the output position adjusting means to adjust the illumination angle of the illumination light by changing the output position of the illumination light.

41. An operation microscope apparatus according to claim 27, wherein:

the slit means comprises a slit member including a plurality of slit hole portions having different slit widths which are formed therein and drive means for driving the slit member to locate one of the plurality of slit hole portions on an optical path of the illumination light; and the control means controls the drive means to adjust the slit width by changing the one of the plurality of slit hole portions, which is located on the optical path, to another one.

42. An operation microscope apparatus according to claim 27, further comprising a first manipulation means for adjusting the illumination angle of the illumination light, wherein the control means specifies a plurality of illumination angles corresponding to the identification information inputted by the input means and controls the illumination optical system in response to a manipulation signal from the first manipulation means to selectively set the plurality of specified illumination angles for the illumination light.

43. An operation microscope apparatus according to claim 27, further comprising a second manipulation means for adjusting the slit width of the slit, wherein the control means specifies a plurality of slit widths corresponding to the identification information inputted by the input means and controls the slit means in response to a manipulation signal from the second manipulation means to selectively set the plurality of specified slit widths for the slit.

44. An operation microscope apparatus according to claim 27, wherein:

each of the plurality of front lenses and a member integrated with each of the plurality of front lenses comprises input instruction means for instructing an input of the identification information which is provided therein; and the input means comprises detecting means for detecting an instruction from the input instruction means and outputs the identification information corresponding to a result obtained by the detection means to the control means.

* * * * *